United States Patent [19]

Baschang et al.

[11] Patent Number: 4,788,182
[45] Date of Patent: Nov. 29, 1988

[54] PHOSPHATIDYL COMPOUNDS, PROCESSES FOR THEIR MANUFACTURE, AND THEIR USE

[75] Inventors: Gerhard Baschang, Bettingen; Bruno Fechtig, Reinach, both of Switzerland; Albert Hartmann, Grenzach, Fed. Rep. of Germany; Bohumir Lukas; Oskar Wacker, both of Basel, Switzerland

[73] Assignee: Ciba-Geigy Corporation, Ardsley, N.Y.

[21] Appl. No.: 113,359

[22] Filed: Oct. 23, 1987

Related U.S. Application Data

[63] Continuation of Ser. No. 757,823, Jul. 22, 1985, abandoned.

[30] Foreign Application Priority Data

Jul. 25, 1984 [CH] Switzerland ............... 3598/84

[51] Int. Cl.$^4$ ................... C07F 9/10; A61K 31/66
[52] U.S. Cl. ................... 514/114; 260/402.5; 260/403; 514/80; 514/91; 514/92; 514/94; 514/119; 548/119; 548/413; 548/414; 558/169; 558/170; 558/172; 558/174
[58] Field of Search ............... 260/403, 402.5; 558/174, 170, 172, 173, 169; 514/77, 119, 114, 170, 171, 80, 91, 94; 548/119, 413, 414

[56] References Cited

U.S. PATENT DOCUMENTS

| | | | |
|---|---|---|---|
| 2,436,699 | 2/1948 | Rose | 260/403 |
| 2,447,715 | 8/1948 | Rose | 260/403 |
| 3,663,235 | 5/1972 | Menz | 99/123 |
| 4,119,714 | 10/1978 | Kuy | 424/199 |
| 4,235,792 | 11/1980 | Hsia | 260/403 |
| 4,254,115 | 3/1981 | Dawidson | 260/403 |
| 4,323,560 | 4/1982 | Baschang | 424/177 |
| 4,372,949 | 2/1980 | Kodama | 424/199 |
| 4,406,890 | 9/1983 | Tarcsay | 424/177 |
| 4,414,204 | 11/1983 | Tarcsay | 424/177 |
| 4,423,038 | 12/1983 | Baschang | 424/177 |
| 4,426,330 | 1/1984 | Sears | 260/403 |
| 4,426,525 | 1/1984 | Hozumi | 546/22 |
| 4,534,899 | 8/1985 | Sears | 260/403 |
| 4,548,923 | 10/1985 | Hartmann | 514/8 |
| 4,607,011 | 8/1986 | Kaplan | 435/131 |
| 4,666,893 | 5/1987 | Tsuchiya | 514/78 |

FOREIGN PATENT DOCUMENTS

| | | |
|---|---|---|
| 72286 | 2/1983 | European Pat. Off. |
| 72111 | 2/1983 | European Pat. Off. |
| 118316 | 9/1984 | European Pat. Off. |
| 1543937 | 1/1970 | Fed. Rep. of Germany |
| 641811 | 3/1984 | Switzerland |
| 2051069 | 1/1981 | United Kingdom |

OTHER PUBLICATIONS

Greenstein, "Chemistry of the Amino Acids," vol. 1, pp. 3-8 (1961).
Chem. Abst. 69: 958906 (1968).
Chem. Abst. 66: 95388g (1967).
Chem. Abst. 71: 123473e (1969).
Kinsey, Journal of Immunological Methods, 65, 295-306 (1983).
Derwent, Abstract of Eur. Pat. 138558
Derwent, Abstract of Jap. 52-087221.
Biochemistry vol. 14, No. 11, pp. 2331-2337, (1975).

*Primary Examiner*—Michael L. Shippen
*Attorney, Agent, or Firm*—Irving M. Fishman

[57] ABSTRACT

Described are phosphatidyl compounds of the formula I $$R^1-T-Y-O-\underset{\underset{OH}{|}}{\overset{\overset{O}{\|}}{P}}-O-\underset{\underset{Z}{|}}{\overset{\overset{W}{|}}{C}}H \qquad (I)$$

in which
R$^1$ represents C$_{3-14}$-alkanoyl, benzoyl, the acyl radical of an α-aminocarboxylic acid that is other than glycine, L-alanine and derivatives thereof having a substituted amino group, and of which the α-amino group may be substituted by lower alkanoyl, lower alkoxycarbonyl or by benzyloxycarbonyl, or the acyl radical of a β-aminocarboxylic acid or an α- or β-hydroxycarboxylic acid,
T represents a group NH that is unsubstituted or is substituted by lower alkyl, or oxygen,
Y represents dimethylene that is unsubstituted or is substituted by free, etherified or amidated carboxy,
W represents hydrogen, and
Z represents a 1,2-dihydroxyethyl, 2-hydroxyethyl or hydroxymethyl group, in which at least one of the hydroxy groups is esterified by an aliphatic C$_{8-30}$-carboxylic acid or is etherified by an aliphatic C$_{8-30}$-alcohol, or each of W and Z represents a hydroxymethyl group that is esterified by an aliphatic C$_{8-30}$-carboxylic acid or is etherified by an aliphatic C$_{8-30}$-alcohol, and their salts, and processes for their manufacture.

The mentioned novel compounds, and structurally related compounds that are likewise described and that belong to the state of the art, are used for the propylaxis and treatment of viral infections.

19 Claims, No Drawings

PHOSPHATIDYL COMPOUNDS, PROCESSES FOR THEIR MANUFACTURE, AND THEIR USE

This application is a continuation of application Ser. No. 757,823 filed 7-22-85, now abandoned.

The invention relates to phosphatidyl compounds of the formula I

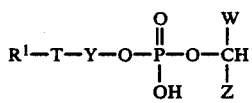

in which $R^1$ represents $C_{3\text{-}14}$-alkanoyl, benzoyl, the acyl radical of an α-aminocarboxylic acid that is other than glycine, L-alanine and derivatives thereof having a substituted amino group, and of which the α-amino group may be substituted by lower alkanoyl, lower alkoxycarbonyl or by benzyloxycarbonyl, or the acyl radical of a β-aminocarboxylic acid or an α- or β-hydroxycarboxylic acid, T represents a group NH that is unsubstituted or is substituted by lower alkyl, or oxygen, Y represents dimethylene that is unsubstituted or is substituted by free, etherified or amidated carboxy, W represents hydrogen, and Z represents a 1,2-dihydroxyethyl, 2-hydroxyethyl or hydroxymethyl group, in which at least one of the hydroxy groups is esterified by an aliphatic $C_{8\text{-}30}$-carboxylic acid or is etherified by an aliphatic $C_{8\text{-}30}$-alcohol, or each of W and Z represents a hydroxymethyl group that is esterified by an aliphatic $C_{8\text{-}30}$-carboxylic acid or is etherified by an aliphatic $C_{8\text{-}30}$-alcohol, and their salts, and to processes for their manufacture.

The invention relates also to the above-mentioned novel compounds of the formula I including certain compounds of which the use in a method for the therapeutic treatment of the human or animal body does not belong to the state of the art, although the compounds themselves do belong to the art, that is to say phosphatidyl compounds of the formula Ia

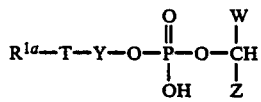

in which $R^{1a}$ represents $C_{2\text{-}22}$-alkanoyl which may be substituted by carboxy, $C_{3\text{-}18}$-alkenoyl, benzoyl, the acyl radical of an α-aminocarboxylic acid of which the α-amino group may be substituted by lower alkyl, lower alkanoyl, lower alkoxycarbonyl or benzyloxycarbonyl, or the acyl radical or a β-aminocarboxylic acid or an α-or β-hydroxycarboxylic acid, and the remaining substituents have the meanings given above, and their salts for use in a method for the therapeutic treatment of the human or animal body and for the manufacture of pharmaceutical preparations and for the industrial manufacture and confectioning of a medicament having antiviral activity.

The invention relates also to the use of the above-mentioned compounds of the formulae I and Ia for the prophylaxis and treatment of viral infections.

$C_{3\text{-}14}$-alkanoyl $R^1$ is especially straight-chain $C_{3\text{-}14}$-alkanoyl, for example propionyl, n-butyryl, lauroyl or myristoyl.

The acyl radical $R^1$ of an α-aminocarboxylic acid that is other than glycine, L-alanine and derivatives thereof having a substituted amino group is especially α-amino-lower alkanoyl that is other than glycine, L-alanine and derivatives thereof having a substituted amino group and that may be substituted by a further amino, lower alkanoylamino, lower alkoxycarbonylamino or benzyloxycarbonylamino group or by guanidino, carboxy, phenoxycarbonyl, benzyloxycarbonyl, benzhydryloxycarbonyl, lower alkoxycarbonyl, carbamoyl, hydroxy, lower alkoxy, lower alkanoyloxy, lower alkoxycarbonyloxy, mercapto, lower alkylthio, (2-amino-2-carboxyethyl)-dithio, phenyl, 4-hydroxyphenyl, imidazol-4-yl or by indol-3-yl, or pyrrolidine-α-carbonyl that is unsubstituted or is substituted by hydroxy, especially γ-hydroxy, lower alkoxy, lower alkanoyloxy or by lower alkoxycarbonyloxy, or 2-(1,3-oxazolidin-5-on-4-yl)acetyl. It is preferably derived from a naturally occurring (L)-α-aminocarboxylic acid, with the exception of glycine and L-alanine, or from the (D)-isomer thereof, especially from L-valine, L-isoleucine, L-phenylalanine, L-threonine, L-cysteine, L-methionine, L-tryptophan, L-glutamine, L-isoglutamine, L-arginine, L-γ-hydroxyproline or more especially from L-tyrosine, L-lysine, L-aspartic acid, L-asparagine, L-histidine, L-glutamic acid, L-serine, L-proline, L-leucine, D-alanine or 2-(1,3-oxazolidin-5-on-4-yl)-acetic acid.

Thus, $R^1$ may represent, for example, the acyl radical of L-tyrosine or of N-lower alkoxycarbonyl- or N-lower alkanoyl-L-tyrosine, the acyl radical of L-leucine or of N-lower alkoxycarbonyl- or N-lower alkanoyl-L-leucine, the acyl radical of L-lysine or of $N^\alpha$-benzyloxycarbonyl-$N^\epsilon$-lower alkoxycarbonyl-L-lysine, the acyl radical of L-glutamic acid or of N-benzyloxycarbonyl-L-glutamic acid α- or γ-lower alkyl ester, the acyl radical of L-serine or of N-lower alkanoyl- or N-lower alkoxycarbonyl-L-serine or the acyl radical of L-proline or of N-lower alkoxycarbonyl-L-proline.

The acyl radical $R^1$ of a β-aminocarboxylic acid is preferably β-amino-lower alkanoyl, especially the acyl radical of β-alanine.

The acyl radical of an α- or β-aminocarboxylic acid is preferably β-amino-lower alkanoyl, especially the acyl radical of β-alanine.

The acyl radical of an α- or β-hydroxycarboxylic acid is especially α- or β-hydroxy-lower alkanoyl which may be substituted by carboxy and/or hydroxy, and is preferably derived from a naturally occurring α- or β-hydroxycarboxylic acid, such as, especially, lactic acid and more especially citric acid.

A carboxy group as a substituent of the radical Y is preferably in the α-position to the radical T. The configuration at the carbon atom carrying this carboxy group is especially (L).

Etherified carboxy as a substituent of Y is especially lower alkoxycarbonyl or benzyloxycarbonyl. Amidated carboxy as a substituent of Y is, for example, carbamoyl.

In a 1,2-dihydroxyethyl radical Z, for example only the terminal hydroxy group, that is to say the 2-hydroxy group, is etherified or, preferably, esterified, or preferably both hydroxy groups are etherified or, preferably, esterified.

An aliphatic $C_{8\text{-}30}$-carboxylic acid preferably has an even number of carbon atoms, especially from 10 to 24, for example from 12 to 24, 16 to 24 or 16 to 22, more especially from 12 to 18, carbon atoms, is branched or, preferably, straight-chained, and is especially a substituted or, preferably, unsubstituted alkanoic or alkenoic acid, the latter preferably having 18 carbon atoms and from 1 to 3 isolated double bonds, for example a naturally occurring fatty acid, such as, especially, palmitic, oleic or stearic acid, or alternatively linoleic or linolenic acid. Examples of an aliphatic $C_{8-30}$-carboxylic acid are also capric, lauric, nervonic or lignoceric acid.

An aliphatic $C_{8-30}$-alcohol preferably has an even number of carbon atoms, especially from 12 to 24, more especially from 16 to 24, and most especially from 16 to 22, carbon atoms, is branched or, preferably, straight-chained and is especially a substituted or more especially, an unsubstituted alkanol or alkenol, examples of substituents that may be mentioned being hydroxy, amino, alkanoylamino or alkenoylamino.

The general terms used hereinbefore and hereinafter, unless otherwise indicated for the specific case in question, preferably have the following meanings:

$C_{2-22}$-alkanoyl $R^{1a}$ is especially straight-chained $C_{2-22}$-alkanoyl, especially straight-chained $C_{2-18}$-alkanoyl, for example acetyl, propionyl, n-butyryl, lauroyl, myristoyl, palmitoyl or stearoyl. Alkanoyl $R^{1a}$ substituted by monomethylamino, trimethylamino or carboxy is preferably correspondingly substituted lower alkanoyl, for example the acyl radical of sarcosine, betaine, succinic acid or glutaric acid.

$C_{3-18}$-alkenoyl $R^{1a}$ is, for example, propenoyl or 2-methylpropenoyl.

The acyl radical of an α-aminocarboxylic acid or of an α- or β-hydroxycarboxylic acid $R^{1a}$ is defined as indicated above for $R^1$ and may additionally represent the acyl radical of glycine, L-alanine or derivatives thereof having an α-amino group substituted by lower alkyl, lower alkanoyl, lower alkoxycarbonyl or benzyloxycarbonyl. A glycine derivative having an amino group substituted by lower alkyl is, for example, betaine.

The general terms used hereinbefore and hereinafter, unless otherwise indicated for the specific case in question, preferably have the following meanings:

The prefix "lower" used hereinbefore and hereinafter denotes radicals having up to and including 7, preferably up to and including 4, carbon atoms.

Lower alkanoyl is, for example, propionyl, butyryl or hexanoyl, especially acetyl.

Lower alkyl is, for example, n-propyl, n-butyl, isobutyl, sec.-butyl, tert.-butyl, also n-pentyl, n-hexyl or n-heptyl, especially methyl, ethyl or isopropyl.

Esterified hydroxy is hydroxy esterified by an organic carboxylic acid or a strong inorganic acid, for example a mineral acid, especially halogen or, preferably, lower alkanoyloxy.

Etherified carboxy is especially lower alkoxycarbonyl or is phenoxycarbonyl, benzyloxycarbonyl or benzhydryloxycarbonyl, each of the latter being unsubstituted or substituted in the aromatic ring.

Amidated carboxy is especially carbamoyl or N-lower alkylcarbamoyl that is unsubstituted or is substituted in the lower alkyl moiety by carboxy or lower alkoxycarbonyl.

Halogen is especially chlorine, bromine or iodine, or, preferably as a phenyl substituent, fluorine.

Lower alkoxy is, for example, ethoxy, propoxy or, preferably, methoxy and in certain cases tert.-butoxy.

As the proton bonded via oxygen to the phosphorus atom is acidic, the compounds of the formula I readily form salts. The compounds of the formula I that contain a basic group, for example amino, can be in the form of internal salts, that is to say in zwitterionic form, at a corresponding pH value. The compounds of the formula I that contain more than one basic group can additionally form acid addition salts with external acids, for example with inorganic acids, such as mineral acids, for example hydrochloric acid, sulphuric acid or phosphoric acid, or with suitable organic carboxylic or sulphonic acids, for example trifluoroacetic, acetic, maleic, fumaric, tartaric, citric, methanesulphonic or 4-toluenesulphonic acid, and with amino acids, such as arginine and lysine.

Compounds of the formula I that contain no basic groups or that contain more acidic groups than basic groups, for example if, in addition to the phosphoric acid group, carboxy groups are also present in the molecule, may form metal or amonium salts, such as alkali metal and alkaline earth metal salts, for example sodium, potassium, magnesium or calcium salts, and ammonium salts with ammonia or suitable organic amines, there being considered for the salt formation especially aliphatic, cycloaliphatic, cyloaliphaticaliphatic or araliphatic primary, secondary or tertiary mono-, di- or poly-amines, and heterocyclic bases, such as lower alkylamines, for example triethylamine, hydroxy-lower alkylamines, for example 2-hydroxyethylamine, bis-(2-hydroxyethyl)-amine, 2-hydroxyethyldiethylamine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and also bases of the pyridine type, for example pyridine, collidine or quinoline.

For isolation or purification it is also possible to use pharmaceutically unacceptable salts. However, only the pharmaceutically acceptable non-toxic salts are used therapeutically and these are therefore preferred.

The novel compounds of the present invention have valuable pharmacological properties.

It was found, surprisingly, according to the invention, that the above-mentioned phosphatidyl compounds of the formula I and their pharmaceutically acceptable salts are outstandingly suitable for the prophylaxis and treatment of viral infections, as is apparent, for example, from tests on animals, as shown in the Examples section. In these animal tests animals, such as mice or guinea pigs, are infected with the most varied types of viruses at a dose that is lethal to all or the great majority of the untreated (control) animals, for example $LD_{80-90}$, and the course of the infection is observed in the untreated control animals in comparison with animals treated with one of the above-mentioned compounds or a salt thereof before, simultaneously with or after infection.

It is found that a prophylactic effect is achieved even when the compounds of the formula I are administered several days up to some weeks, for example four weeks, before infection, and that a therapeutic effect is still achieved when the compounds are administered several days, for example one week, after infection.

Also noteworthy is the broad viral spectrum against which the above-mentioned compounds are effective.

The compounds of the formula I can be used especially for the prophylaxis and treatment of diseases caused by the viruses specified below [for nomenclature see J. L. Melnick, Prog. med. Virol. 26, 214–232 (1980) and 28, 208–221 (1982)]:

DNA viruses with cubic symmetry and naked nucleocapsid, DNA viruses with encapsulated virion and RNA viruses with cubic symmetry and those with helical symmetry of the capsid.

The compounds of the formula I are preferably used in the case of DNA viruses with encapsulated virion and cubic symmetry of the capsid, in the case of RNA viruses with cubic symmetry of the capsid and naked virion and in the case of RNA viruses with helical symmetry of the capsid, in which the nucleocapsid capsule is positioned at the surface membrane, but also in the case of adenoviridae, poxviridae and coronaviridae, such as, especially, human corona viruses.

The compounds of the formula I are used especially in the case of herpesviridae, picornaviridae and myxo viruses, but also in the case of mastadeno viruses, such as, especially, human adeno viruses, in the case of chordopoxvirinae, such as, chiefly, orthopox viruses, such as especially, for example, vaccinia viruses, in the case of reoviridae, above all (especially human) rota viruses, and in the case of caliciviridae and rhabdoviridae, such as, especially, vesiculo viruses in humans and also in horses, cattle and pigs.

The compounds of the formula I are used chiefly in the case of alpha-herpesvirinae, such as varicella viruses, for example human varicella-zoster viruses, rhino viruses, cardio viruses and ortho-myxoviridae, but also in the case of beta-herpesvirinae, such as, especially, human cytomegalo viruses, in the case of aphtho viruses, especially aphtho viruses in animals with cloven hooves, such as, especially, cattle, and in the case of para-myxoviridae, such as, especially, pneumo viruses, for example respiratory syncytial viruses in humans, and such as, also, morbilli viruses or para-myxo viruses, such as para-influenza viruses, for example human para-influenza viruses, including Sendai viruses, and in the case of arbo viruses or vesiculo viruses, for example *Vesicular stomatitis* viruses.

The compounds of the formula I are used more especially in the case of simplex viruses, for example human Herpes simplex viruses of types 1 and 2, in the case of human encephalomyocarditis viruses, in the case of influenza viruses, such as, especially, influenza A and influenza B viruses and, most particularly, in the case of the viruses mentioned in the Examples.

The compounds of the formula I can be used according to the invention by administering them enterally or parenterally, especially together with suitable adjuncts or carriers. They are preferably applied to the mucous membranes, for example intranasally, rectally or vaginally, or to the conjunctiva of the eye, or orally. However, the antiviral effect also occurs in the case of administration by other routes, for example subcutaneously, intravenously or intramuscularly, or in the case of application to normal skin.

The dosage of the active ingredient depends, inter alia, on the species of warm-blooded animal, the organism's resistance, the method of administration and the type of virus. There is relatively little relationship between the dosage and the effect.

For prevention, a single dose of from approximately 0.01 mg to approximately 25 mg, preferably from 0.05 to 7 mg, for example 0.5 mg, of active ingredient is administered to a warm-blooded animal of approximately 70 kg body weight, for example a human. The prophylactic effect of this dose lasts for several weeks. If necessary, for example when there is an increased risk of infection, the administration of this dose can be repeated.

The therapeutic dose. for warm-blooded animals of approximately 70 kg body weight is from 0.1 mg to 50 mg, preferably from 0.1 to 10 mg, for example 5 mg, especially in the case of oral administration. The dose in the case of topical, especially intranasal, administration is up to ten times lower. If necessary, the administration of the compounds of the formula I can be repeated until there is an improvement in the illness. Often, however, a single administration is sufficient.

The invention relates especially to the phosphatidyl compounds of the formula I in which T represents a group NH and/or in which W represents hydrogen and Z represents a 1,2-dihydroxyethyl group in which at least one of the hydroxy groups is esterified by an aliphatic $C_{8-30}$-carboxylic acid, and their salts.

Preferred are compounds of the formula I in which Y represents dimethylene that is unsubstituted or is substituted by carboxy, lower alkoxycarbonyl or carbamoyl, W represents hydrogen and Z represents 1,2-dihydroxyethyl, in which either only the 2-hydroxy group or both hydroxy groups is (are) esterified by a $C_{12-24}$-alkanoic or -alkenoic acid, or each of W and Z represents a hydroxymethyl group esterified by a $C_{12-14}$-alkanoic or -alkenoic acid, and their salts.

Especially preferred are the above-mentioned compounds of the formula I in which $R_1$ represents the acyl radical of an alkanoic acid having up to 12 carbon atoms that is unsubstituted or is substituted by one or two amino groups, one or two carboxy groups, hydroxy, mercapto, lower alkylthio, phenyl, 4-hydroxyphenyl, carbamoyl, guanidino, 3-indolyl, 4-imidazolyl or (2-amino-2-carboxyethyl)-dithio, with the exception of the acyl radicals of glycine, L-alanine and the derivatives thereof having a substituted amino group, or a benzoyl or prolyl radical, and their salts.

Especially preferred are the above-mentioned compounds of the formula I in which $R^1$ represents the acyl radical of one of those 20 amino acids that are regularly present in proteins, with the exception of glycine and L-alanine, or the acyl radical of lactic acid or citric acid, and their salts.

Especially preferred are the above-mentioned compounds of the formula I in which $R^1$ represents the acyl radical of L-valine, L-serine, L-threonine, L-cysteine, L-methionine, L-tyrosine or citric acid, T represents a group NH, Y represents unsubstituted or carboxy-substituted dimethylene, W represents hydrogen and Z represents 1,2-dihydroxyethyl, in which each hydroxy group is esterified by a straight-chained $C_{16-24}$-alkanoic or -alkenoic acid having an even number of carbon atoms, and their salts.

More especially preferred are the above-mentioned compounds of the formula I in which $R^1$ represents benzoyl or the acyl radical of L-tyrosine, L-lysine, L-aspartic acid, L-asparagine, L-histidine, -glutamic acid, L-serine, L-proline, L-leucine, D-alanine or 2-(1,3-oxazolidin-5-on-4-yl)-acetic acid, it being possible for amino groups present in these acyl radicals to be substituted at the nitrogen atom by tert.-butoxycarbonyl, benzyloxycarbonyl or lower alkanoyl and for carboxy groups present to be esterified by a lower alkanol, T represents a group NH, Y represents dimethylene that is unsubstituted or is substituted by carboxy or lower alkoxycarbonyl, W represents hydrogen and Z represents a 1,2-dihydroxyethyl, 2-hydroxyethyl or hydroxymethyl group in which at least one of the hydroxy groups is esterified by a $C_{10-18}$-alkanoic acid or a $C_{18}$-alkenoic acid, or each of W and Z represents a hydroxymethyl group that is esterified by a $C_{10-18}$-alkanoic acid or a $C_{18}$-alkenoic acid, and their salts.

Preferred are also those compounds of the formula I in which each of W and Z represents a hydroxymethyl group that is esterified by a $C_{18}$-alkenoic acid or by a straight-chained $C_{12}$-$C_{18}$-alkanoic acid, and their salts.

Especially preferred are the pharmaceutically acceptable salts of the above-mentioned compounds of the formula I.

Preferred above all are the compounds of the formula I described in the Examples, and their salts.

The phosphatidyl compounds of the formula I and their salts are manufactured by methods known per se. They are obtained, for example, as follows:

(a) a compound of the formula II

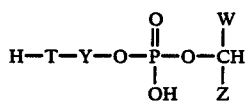

(II)

in which the substituents have the meanings given above, functional groups present in a compound of the formula II, with the exception of the group that participates in the reaction, being, if necessary, in protected form, or a reactive derivative thereof, is reacted with a compound of the formula III $$R^1\text{—OH} \qquad (III)$$

in which $R^1$ has the meaning given above, functional groups present in a compound of the formula III, with the exception of the group that participates in the reaction, being, if necessary, in protected form, or with a reactive carboxylic acid derivative thereof, and any protecting groups present are removed, or (b) a compound of the formula IV

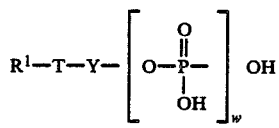

(IV)

in which w represents 0 or 1 and $R^1$, T and Y have the meanings given above, functional groups present in a compound of the formula IV, with the exception of the group that participates in the reaction, being, if necessary, in protected form, or a reactive derivative thereof, is reacted with a compound of the formula V

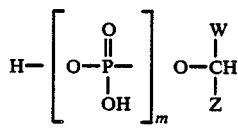

(V)

in which W and Z have the meanings given above, functional groups oresent in a compound of the formula V, with the exception of the group that participates in the reaction, being, if necessary, in protected form, and, if w represents 0 in the reactant of the formula IV, m represents 1 or, if w represents 1, m represents 0, or with a reactive derivative of a compound of the formula V, and any protecting groups present are removed, or (c) a compound of the formula VI

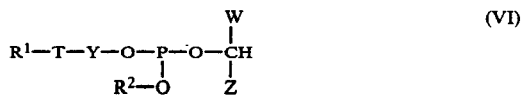

(VI)

in which $R^2$ represents hydrogen or a protecting group and the other substituents have the meanings given above, functional groups present in a compound of the formula VI, with the exception of the group that participates in the reaction, being, if necessary, in protected form, or a tautomer of a compound of the formula VI, is oxidised with an oxidising agent, and any protecting groups present are removed, or (d) a compound of the formula VII

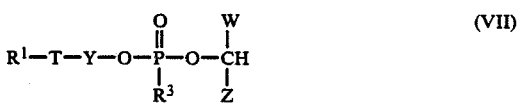

(VII)

in which $R^3$ represents halogen and the other substituents have the meanings given above, functional groups present in a compound of the formula VII, with the exception of the group that participates in the reaction, being, if necessary, in protected form, is hYdrolysed, and any protecting groups are removed, or (e) a compound of the formula VIII

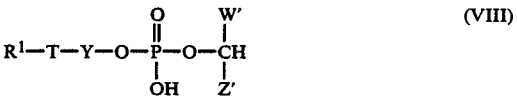

(VIII)

in which W′ represents hydrogen and Z′ represents 1,2-dihydroxyethyl, 2-hydroxyethyl, hydroxymethyl or 1,2-dihydroxyethyl, in which one of the two hydroxy groups is esterified by an aliphatic $C_{8-30}$-carboxylic acid or is etherified by an aliphatic $C_{8-30}$-alcohol, or one of the radicals W′ and Z′ represents hydroxymethyl and the other radical W′ or Z′ represents free hydroxymethyl or hydroxymethyl that is esterified by an aliphatic $C_{8-30}$-carboxylic acid or is etherified by an aliphatic $C_{8-30}$-alcohol, and $R^1$, T and Y have the meanings given above, functional groups present in a compound of the formula VIII, with the exception of the group that participates in the reaction, being, if necessary, in protected form, or a reactive derivative thereof, is esterified by an aliphatic $C_{8-30}$-carboxylic acid or a reactive derivative thereof, or is etherified by an aliphatic $C_{8-30}$-alcohol or a reactive derivative thereof, and any protecting groups present are removed, or (f) a compound of the formula IX

(IX)

in which X represents a nucleophilic leaving group and the other substituents have the meanings given above, functional groups present in a compound of the formula IX, with the exception of the group that participates in the reaction, being, if necessary, in protected form, is reacted with a compound of the formula X $$R^1-T-H \qquad (X)$$

in which the substituents have the meanings given above, functional groups present in a compound of the formula X, with the exception of the group that participates in the reaction, being, if necessary, in protected form, or with a reactive derivative thereof, and any protecting groups present are removed, or (g) in a compound of the formula I in which the substituents have the meanings given above, it being necessary for at least one functional group in a compound of the formula I to be protected by a readily removable protecting group, the protecting group(s) is (are) removed, or (h) for the manufacture of a compound of the formula I in which W represents hydrogen and Z represents a 1,2-dihydroxyethyl group in which the 2-hydroxy group is esterified by an aliphatic $C_{8-30}$-carboxylic acid, a compound of the formula I in which W represents hydrogen and Z represents a 1,2-dihydroxyethyl group in which both hydroxy groups are esterified by an aliphatic $C_{8-30}$-carboxylic acid, is reacted with an enzyme that is suitable for the regioselective removal of the radical that esterifies the 1-hydroxy group, and, when one of the above-mentioned process variants a–h) has been carried out, in order to manufacture a salt if necessary a compound of the formula I is converted into a salt, or in order to convert a compound of the formula I or a salt thereof into a different compound of the formula I or into a salt thereof, an amino or hydroxy group contained in the radical $R^1$ is acylated or a carboxy group contained in the radical $R^1$ or Y is esterified or amidated.

The above-mentioned process variants are described in detail below:

Process a

The group that takes part in the reaction in a compound of the formula II is the group H-T. If T represents NH optionally substituted by lower alkyl, and if the reaction is suitably carried out, only other amino groups present in the molecule of the formula II and carboxy groups that may be present need to be protected. The protection of hydroxy groups or mercapto groups is optional.

If T represents oxygen, advantageously all other hydroxy groups present in the molecule of the formula II as well as free amino, lower alkylamino, mercapto and carboxy and, if appropriate, other functional groups, are protected.

Protecting groups and the manner in which they are introduced and removed are described, for example, in "Protective Groups in Organic Chemistry", Plenum Press, London, New York 1973, and in "Methode'n der organischen Chemie", Houben-Weyl, 4th Edition, Vol. 15/1, Georg-Thieme-Verlag, Stuttgart 1974 and in Theodora W. Greene, "Protective Groups in Organic Synthesis", John Wiley & Sons, New York 1981. It is characteristic of protecting groups that they can be readily removed, that is to say without undesired secondary reactions taking place, for example by solvolysis, reduction, photolysis or alternatively under physiological conditions.

Hydroxy-protecting groups are, for example, acyl radicals, such as optionally substituted, for example halo-substituted, lower alkanoyl, such as 2,2-dichloroacetyl, or acyl radicals of carbonic acid semi-esters, especially tert.-butoxycarbonyl, optionally substituted benzyloxycarbonyl, or diphenylmethoxycarbonyl, for example 4-nitrobenzyloxycarbonyl, or 2-halo-lower alkoxycarbonyl, such as 2,2,2-trichloroethoxycarbonyl, also trityl or formyl, or organic silyl or stannyl radicals, also readily removable etherifying groups, such as tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also optionally substituted 1-phenyl-lower alkyl, such as optionally substituted benzyl or diphenylmethyl, there being suitable as substituents of the phenyl radicals, for example, halogen, such as chlorine, lower alkoxy, such as methoxy, and/or nitro.

Carboxy groups are customarily protected in esterified form, such ester groupings being readily cleavable under mild conditions. Carboxy groups protected in this manner contain as esterifying groups especially lower alkyl groups that are branched in the 1-position or suitably substituted in the 1- or 2-position. Preferred carboxy groups in esterified form are, inter alia, tert.-lower alkoxycarbonyl, for example tert.-butoxycarbonyl, arylmethoxycarbonyl having one or two aryl radicals, these being phenyl radicals optionally mono- or poly-substituted, for example, by lower alkyl, such as tert.-lower alkyl, for example tert.-butyl, lower alkoxy, such as methoxy, hydroxy, halogen, for example chlorine, and/or by nitro, such as benzyloxycarbonyl optionally substituted, for example, as mentioned above, for example 4-methoxybenzyloxycarbonyl or 4-nitrobenzyloxycarbonyl, or diphenylmethoxycarbonyl optionally substituted, for example, as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group represents benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, represents an aliphatic, araliphatic, cycloaliphatic or aromatic hydrocarbon radical that is optionally substituted, for example, by lower alkyl, lower alkoxy, aryl, halogen and/or by nitro, such as corresponding optionally substituted lower alkyl, phenyl-lower alkyl, cycloalkyl or phenyl, for example 2-tri-lower alkylsilylethoxycarbonyl, 2-trimethylsilylethoxycarbonyl or 2-(di-n-butylmethylsilyl)-ethoxycarbonyl, or 2-triarylsilylethoxycarbonyl, such as 2-triphenylsilylethoxycarbonyl.

The organic silyl or stannyl radicals mentioned hereinbefore and hereinafter preferably contain lower alkyl, especially methyl, as substituent of the silicon or tin atoms. Corresponding silyl or stannyl group are especially tri-lower alkylsilyl, especially trimethylsilyl, also dimethyl-tert.-butylsilyl, or correspondingly substituted stannyl, for example tri-n-butylstannyl.

Preferred protected carboxy groups are tert.-lower alkoxycarbonyl, such as tert.-butoxycarbonyl, and especially benzyloxycarbonyl or diphenylmethoxycarbonyl optionally substituted, for example, as mentioned above, such as 4-nitrobenzyloxycarbonyl, and more especially 2-(trimethylsilyl)-ethoxycarbonyl.

A protected amino grop can be, for example, in the form of a readily cleavable acylamino, arylmethylamino, etherified mercaptoamino, 2-acyl-lower alk-1-enylamino, silylamino or stannylamino group or in the form of an azido group.

In a corresponding acylamino group, acyl is, for example, the acyl radical of an organic carboxylic acid having, for example, up to 18 carbon atoms, especially an alkanecarboxylic acid optionally substituted, for example, by halogen or aryl, or of benzoic acid optionally substituted, for example, by halogen, lower alkoxy or nitro, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl optionally substituted, for example, by halogen, lower alkoxy or by nitro, for example benzoyl, 4-chlorobenzoyl, 4-methoxbbenzoyl or 4-nitrobenzoyl, or lower alkoxycarbonyl that is branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals that are preferably phenyl optionally mono- or poly-substituted, for example, by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroylmethoxycarbonyl in which the aroyl group preferably represents benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)ethoxycarbonyl in which each of the substituents, independently of the others, represents an aliphatic, araliphatic, cycloaliphatic or aromatic hydrocarbon radical that has up to 15 carbon atoms and is optionally substituted, for example, by lower alkyl, lower alkoxy, aryl, halogen or by nitro, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethylsilyl)ethoxycarbonyl, or 2-triarylsilylethoxycarbonyl, such as 2-triphenylsilylethoxycarbonyl.

Further acyl radicals coming into consideration as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, di-(phenyl-lower alkyl)-phosphoryl that is optionally substituted, for example, by nitro, for example dibenzylphosphoryl or di-(4-nitrobenzyl)-phosphoryl, optionally substituted phenoxyphenylphosphonyl, for example phenoxyphenylphosphonyl, di-lower alkylphosphinyl, for example diethylphosphinyl, or optionally substituted diphenylphosphinyl, for example diphenylphosphinyl.

In an arylmethlamino group that is a mono-, dior especially tri-arylmethylamino group, the aryl radicals are especially optionally substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl that is optionally substituted, for example, by lower alkyl, such as methyl or tert.-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that may be used as an amino-protecting group, acyl is, for example, the corresponding radical of a lower alkanecarboxylic acid, of benzoic acid that is optionally substituted, for example, by lower alkyl, such as methyl or tert.-butyl, lower alkoxy, such as methoxy, halogen, such as chlorine, and/or by nitro, or especially of a carbonic acid semi-ester, such as a carbonic acid lower alkyl semi-ester. Corresponding protecting groups are especially 1-lower alkanoylprop-1-en-2-yl, for example 1-acetyl-prop-1-en-2-yl, or 1-lower alkoxycarbonylprop-1-en-2-yl, for example 1-ethoxycarbonylprop-1-en-2-yl.

An amino group can also be protected in protonated form; as corresponding anions there come into consideration especially those of strong inorganic acids, such as hydrohalic acids, for example the chlorine or bromine anion, or organic sulphonic acids, such as p-toluenesulphonic acid.

Preferred amino-protecting groups are acyl radicals of carbonic acid semi-esters, especially tert.-butoxycarbonyl, or benzyloxycarbonyl or diphenylmethoxycarbonyl each of which is optionally substituted, for example as indicated, for example 4-nitrobenzyloxycarbonyl, or 2-halo-lower alkoxycarbonyl, such as 2,2,2trichloroethoxycarbonyl, also trityl or formyl.

A mercapto group, such as, for example, in cysteine, can be protected especially by S-alkylation with optionally substituted alkyl radicals, by thioacetal formation, S-acylation or by establishing asymmetrical disulphide groupings. Preferred mercapto-protecting groups are, for example, benzyl optionally substituted in the phenyl radical, for example by methoxy or nitro, such as 4-methoxybenzyl, diphenylmethyl optionally substituted in the phenyl moiety, for example by methoxy, such as 4,4'-dimethoxydiphenylmethyl, triphenylmethyl, trimethylsilyl, benzylthiomethyl, tetrahydropyranyl, acylaminomethyl, benzoyl, benzyloxycarbonyl or aminocarbonyl, such as ethylaminocarbonyl.

The reaction is preferably carried out by reacting the compound of the formula III in the form of an activated carboxylic acid derivative with the compound of the formula II, it also being possible for the activation of the carboxylic acid of the formula III to be carried out in situ in the presence of the compound of the formula II.

Activated carboxylic acid derivatives of a compound of the formula III are especially reactive activated esters or reactive anhydrides, also reactive cyclic amides; reactive derivatives of acids of the formula III can also be formed in situ.

Activated esters of acids are especially esters that are unsaturated at the linking carbon atom of the esterifying radical, for example of the vinyl ester type, such as actual vinyl esters (which can be obtained, for example, by transesterification of a corresponding ester with vinyl acetate; activated vinyl ester method), carbamoylvinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-disubstituted amidino esters (which can be obtained, for example, by treating the corresponding acid with a suitable N,N'-disubstituted carbodiimide, for example N,N'-dicyclohexyl carbodiimide; carbodiimide method), or N,N-disubstituted amidino esters (which can be obtained, for example, by treating the corresponding acid with an N,N-disubstituted cyanamide; cyanamide method), suitable aryl esters, especially phenyl esters suitably substituted by electron-attracting substituents (which can be obtained, for example, by treating the corresponding acid with a suitably substituted phenol, for example 4nitrophenol, 4-methylsulphonylphenol, 2,4,5trichlorophenol, 2,3,4,5,6-pentachlorophenol or 4phenyldiazophenol, in the presence of a condensation agent, such as N,N'-dicyclohexyl carbodiimide; activated aryl esters method), cyanomethyl esters (which can be obtained, for example, by treating the corresponding acid with chloroacetonitrile in the presence of a base; cyanomethyl esters method), thioesters, especially phenylthioesters optionally substituted, for example, by nitro (which can be obtained, for example, by treating the corresponding acid with thiophenols that are optionally substituted, for example, by nitro, inter alia with the aid of the anhydride or carbodiimide method; activated thioesters method), or amino or amido esters (which can be obtained, for example, by treating the corresponding acid with an N-hydroxyamino or N-hydroxyamido compound, for example N-hydroxysuccinimide, N-hydroxypiperidine, N-hydroxyphthalimide or ]-hydroxybenzotriazole, for example according to the anhydride or carbodiimide method; activated N-hydroxyesters method), or silyl esters (which can be obtained, for example, by treating the corresponding acid with a silylating agent, for example hexamethyldisilazane, and which react readily with hydroxy groups but not with amino groups).

Anhydrides of acids of the formula III may be symmetrical or, preferably, mixed anhydrides of these acids, for example anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and the treatment of the latter with nitrous acid; azide method), anhydrides with carbonic acid semiderivatives, such as with corresponding esters, for example carbonic acid lower alkyl semi-esters (which can be obtained, for example, by treating the corresponding acid with haloformic acid lower alkyl esters, such as chloroformic acid lower alkyl esters, or with a 1-lower alkoxycarbonyl-2-lower alkoxy-1,2-dihydroquinoline, for example 1-lower alkoxycarbonyl-2-ethoxy1,2-dihydroquinoline; mixed 0-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an optionally substituted lower alkanecarboxylic acid halide or phenylalkanecarboxylic acid halide, for example phenylacetic acid chloride, pivalic acid chloride or trifluoroacetic acid chloride; mixed carboxylic acid anhydrides method) or with organic sulphonic acids (which can be obtained, for example, by treating a salt, such as an alkali metal salt, of the corresponding acid with a suitable organic sulphonic acid halide, such as lower alkanesulphonic acid chloride or arylsulphonic acid chloride, for example methane- or p-toluene-sulphonic acid chloride; mixed sulphonic acid anhydrides method), and symmetrical anhydrides (which can be obtained, for example, by condensing the corresponding acid in the presence of a carbodiimide or of 1-diethylaminopropine; symmetrical anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5dimethylpyrazole (which can be obtained, for example, by way of the acid hydrazide by treatment with acetylacetone; pyrazolide method).

As mentioned, derivatives of acids of the formula III can also be formed in situ. For example, N,N'-disubstituted amidino esters can be formed in situ by reacting a mixture of the starting material of the formula II and the acid of the formula III in the presence of a suitable N,N-disubstituted carbodiimide, for example N,N'-dicyclohexyl carbodiimide. It is also possible to form amino or amido esters of acids of the formula III in the presence of the starting material of the formula II to be acylated by reacting a mixture of the corresponding acid and amino starting materials in the presence of an N,N'-disubstituted carbodiimide, for example N,N'-dicyclohexyl carbodiimide, and an N-hydroxyamine or N-hydroxyamide, for example N-hydroxysuccinimide, optionally in the presence of a suitable base, for example 4-dimethylaminopyridine.

Alternatively, process variant a) can be carried out by reacting the acid III with a reactive derivative of a compound of the formula II.

A derivative of a compound of the formula II in which the radical H-T is the group NH and in which the amino group participating in the reaction is in reactive form can be manufactured, for example, by reaction with a phosphite, for example diethyl chlorophosphite, 1,2-phenylene chlorophosphite, ethyl dichlorophosphite, ethylene chlorophosphite or tetraethyl pyrophosphite. A reactive form of a compound of the formula II is, for example, also a carbamic acid halide or an isocyanate, in a compound of the formula II the amino group participating in the reaction being bonded to halocarbonyl, for example chlorocarbonyl, or being in the form of an isocyanate group; in the latter case only compounds of the formula I that carry a hydrogen atom at the nitrogen atom of the amide group formed by the reaction can be obtained.

A derivative of a compound of the formula II in which the group H-T is hydroxy in reactive form is, for example, a halide. In this case it is also possible, for example, to react a metal salt, such as an alkali metal salt, preferably a caesium salt, of a carboxylic acid of the formula III with the mentioned halide.

The reaction can be carried out in a manner known per se, the reactions conditions depending especially on whether and how the carboxy group that participates in the reaction is activated, customarily in the presence of a suitable solvent or diluent or a mixture thereof, and, if necessary, in the presence of a condensation agent which, for example, if the carboxy group that participates in the reaction is present in the form of an anhydride, may also be an acid-binding agent, while cooling or heating, for example in a temperature range of from approximately −30° C. to approximately +150° C., in a closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-N'(3-dimethylaminopropyl)-carbodiimide, suitable carbonyl compounds, for example carbonyldiimidazole, or 1,2-oxazolium compounds, for example 2-ethyl-5-phenyl1,2-oxazolium-3'-sulphonate and 2-tert.-butyl-5-methylisoxazolium perchlorate, or a suitable acylamino compound, for example 2-ethoxy-1-ethoxycarbonyl-1,2dihydroquinoline. Customary acid-binding condensation agents are, for example, alkali metal carbonates or bicarbonates, for example sodium or potassium carbonate or bicarbonate (customarily together with a sulphate), or organic bases, such as, customarily, sterically hindered tri-lower alkylamines, for example N,N-diisopropyl-N-ethylamine.

The removal of the protecting groups, for example the carboxy-, amino-, hydroxy- or mercapto-protecting groups, is carried out in a manner known per se, for example by means of solvolysis, especially hydrolysis, alcoholysis or acidolysis, or by means of reduction, especially hydrogenolysis or chemical reduction, optionally in stages or simultaneously, it also being possible to use enzymatic methods.

Thus, tert.-lower alkoxycarbonyl, or lower alkoxycarbonyl substituted in the 2-position by an organic silyl group or in the 1-position by lower alkoxy or lower alkylthio, or optionally substituted diphenylmethoxycarbonyl can be converted into free carboxy, for example, by treatment with a suitable acid, such as formic acid or trifluoroacetic acid, optionally with the addition of a nucleophilic compound, such as phenol or anisole. Optionally substituted benyloxycarbonyl can be freed, for example, by hydrogenolysis, that is to say by treatment with hydrogen in the presence of a metallic hydrogenation catalyst, such as a palladium catalyst. In addition, suitably substituted benzyloxycarbonyl, such as 4-nitrobenzyloxycarbonyl, can be converted into free carboxy by chemical reduction, for example by treatment with an alkali metal dithionite, for example sodium dithionite, or with a reducing metal, for example zinc, or a reducing metal salt, such as a chromium(II) salt, for example chromium(II) chloride, usually in the presence of an agent that yields hydrogen and that, together with the metal, is capable of producing nascent hydrogen, such as an acid, especially a suitable carboxylic acid, such as a lower alkanecarboxylic acid optionally substituted, for example, by hydroxy, for example acetic acid, formic acid, glycolic acid, diphenylglycolic acid, lactic acid, mandelic acid, 4-chloromandelic acid or tartaric acid, or an alcohol or thiol, water preferably being added. By treatment with a reducing metal or metal salt, as described above, it is also possible to convert 2-halo-lower alkoxycarbonyl (optionally after conversion of a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide. acetamide.

A protected amino group is freed in a manner known per se and, depending on the nature of the protecting groups, by various methods, but preferably by solvolysis or reduction. 2-halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with a alkali metal dithionite, for example sodium dithionite. Optionally substituted diphenylmethoxycarbonylamino, tert.-lower alkoxycarbonylamino or 2-trisubstituted silylethoxycarbonylamino can be cleaved by treatment with a suitable acid, for example formic acid or trifluoroacetic acid, optionally substituted benzyloxycarbonylamino can be cleaved, for example, by hydrogenolysis, that is to say by treatment with hydrogen in the presence of a suitable hydrogenation catalyst, such as a palladium catalyst, optionally substituted triarylmethylamino or formylamino can be cleaved, for example, by treatment with an acid, such as a mineral acid, for example hydrochloric acid, or an organic acid, for example formic, acetic or trifluoroacetic acid, optionally in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and by subsequent solvolysis, such as alcoholysis or hydrolysis, of the resulting condensation product. An amino group protected by 2-substituted silylethoxycarbonyl can also be converted into the free amino group by treatment with a salt of hydrofluoric acid yielding fluoride anions, as indicated above in connection with the freeing of a correspondingly protected carboxy group.

Amino protected in the form of an azido group is converted into free amino, for example, by reduction, for example by catalytic hydrogenation with hydrogen in the presence of a hydrogenaton catalyst, such as platinum oxide, palladium or Raney nickel, or alternatively by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively while cooling or heating.

A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group etherified by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Two hydroxy groups that are together protected by a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid.

If several protected functional groups are present, the protecting groups are preferably so chosen that more than one such group can be removed at the same time, for example by acidolysis, such as by treatment with trifluoroacetic acid or formic acid, or by reduction, such as by treatment with zinc and acetic acid, or by hydrogen and a hydrogenation catalyst, such as a palladium-on-carbon catalyst. Process b:

A reactived derivative of a compound of the formula IV in which w represents 1, or of a compound of the formula V in which m represents 1 is, for example, a mono- or bis-anhydride with a strong acid, especially a mineral acid, such as, preferably, a hydrohalic acid, such as, especially, hydrochloric acid. The second acidic phosphoric acid group may be present as such, in the form of an anhydride as described above, or in esterified form, there being preferred as esterifying radicals those that can be removed again regioselectively once the reaction between compounds IV and V is complete, for example the methyl ester group, which can be removed, for example, by alkaline hydrolysis or preferably using lithium chloride, or especially hydrogenolytically removable radicals, for example benzyl or phenyl ester radicals, it being possible for benzyl ester radicals to be removed, for example, in the presence of palladium catalysts, such as palladium-on-carbon, and for phenyl ester groups to be removed, for example, in the presence of platinum or mixed platinum/palladium catalysts.

The formation of reactive phosphoric acid derivatives may also be effected in situ in the presence of compounds that are capable of forming with phosphoric acid or the monoesters thereof, at least intermediately, reactive compounds having an anhydride- or enol ester-like character, for example in the presence of p-toluenesulphonic acid chloride, cyanuric chloride, N-alkyl-5-phenylisoxazolium salts, ethoxyactylene or, preferably, trichloroacetonitrile or, especially, a carbodiimide, such as, especially, dicyclohexyl carbodimide. For example, a phosphoric acid monoester of the formula IV or V in which w or m, respectively, represents 1 is reacted with excess alcohol of the formula IV or V, in which w or m, respectively, represents O, in the presence of a multiple of, for example 5 times, the molar amount of dicyclohexyl carbodiimide, and in the presence or absence of a tertiary amine.

If both acidic groups in a phosphoric acid monoester are present in the form of an anhydride with a hydrohalic acid, it is possible initially to obtain, in addition to the triester, also phosphoric acid diester halides which can then be hydrolysed to form diesters using water, or water-yielding agents, or by heating with tertiary alcohols, such as tert.-butanol or tetrahydropyranol.

If a phosphoric acid monoester dihalide, for example a phosphoric acid monoester dichloride, is used as starting material, the reaction is preferably carried out in the presence of a tertiary amine, such as pyridine, lutidine or quinoline, additional activation of the ester chloride being effected by dimethylformamide.

A preferred embodiment of process b is the reaction of a phosphoric acid monoester dichloride with the corresponding alcohol in the presence of a tertiary amine, followed by the hydrolysis of the phosphoric acid diester halide initially obtained.

In a reactive derivative of a compound of the formula IV or V in which w or m represents O, the hydroxy group that takes part in the reaction is in reactive esterified form.

Reactive esterified hydroxy is, for example, hydroxy esterified by a strong inorganic or organic acid, such as a mineral acid, for example a hydrohalic acid, such as hydrochloric, hydrobromic or hydriodic acid, also sulphuric acid, or a halosulphuric acid, for example fluorosulphuric acid, or hydroxy esterified by a strong organic sulphonic acid, such as an optionally halo-substituted, such as fluorine-substituted, lower alkanesulphonic acid or an aromatic sulphonic acid, for example a benzenesulphonic acid optionally substituted by lower alkyl, such as methyl, halogen, such as bromine, and/or by nitro, for example a methanesulphonic, trifluoromethanesulphonic or p-toluenesulphonic acid, preferably a chloride, bromide or iodide.

The reaction can be carried out in such a manner that a reactive phosphoric acid derivative of the formula IV or V is reacted with an alcohol of the formula V or IV, respectively, in non-activated form, or by reacting a reactive esterified alcohol of the formula IV or V with a phosphoric acid derivative of the formula V or IV, respectively in non-activated form, or with a reactive salt thereof.

In view of the intended nucleophilic substitution reaction, there are used as salts of compounds of the formula IV or V especially reactive salts, for example salts, such as silver salts, that are capable of forming a sparingly soluble precipitate with the nuclophilic leaving group in the reactant, for example one of the above-mentioned halide ions, or salts having a large cation, for example caesium salts, in which the nucleophilicity of the phosphate radical i increased. In order to increase the nucleophilicity of the phosphate radical, the ion of opposite charge may also be removed spatially, for example by the addition of complex formers, such as crown ethers, for example 18-crown-6. When using 18-crown-6 it is possible to carry out the reaction using a potassium salt.

A preferred embodiment of process b is the reaction of the silver salt of a phosphoric acid monoester of the formula IV or V in which one of the two acidic groups is protected by a readily removable protecting group, for example one of those described above, for example in the form of the benzyl or phenyl ester, with a reactive alcohol of the formula V or IV, respectively, in which the OH group has been replaced by chlorine, bromine or iodine. When the reaction is complete, the protecting group is removed, for example a benzyl or phenyl ester protecting group is removed by hydrogenation as described above.

Process c

Most of the compounds of the formula VI in which $R^2$ represents hydrogen are in tautomeric form, in which a proton is bonded directly to phosphorus. The oxidation may be carried out, for example, using aqueous potassium permanganate at temperatures in the region of 0° C. Also suitable as oxidising agents in aqueous medium are alkali metal iodates, periodates and hypochlorites, peracetic acid, N-chloro-4-methylbenzenesulphonic acid amide, etc.

Protecting groups $R^2$ are, for example, those mentioned under process b.

Process d

In a compound of the formula VII, $R^3$ represents halogen, such as bromine or iodine, but especially chlorine.

The hydrolysis is carried out using water or a water-yielding agent, preferably at elevated temperature, for example at from 30° to 95° C.

The starting materials are, for example, as described for process b, or are obtainable by chlorination of the corresponding phosphorous acid diesters, for example using elemental chlorine.

Process e

As protecting groups or as reactive carboxylic acid derivatives there may be used, for example, those mentioned for process a. As reactive alcohol derivatives there are used alcohols of which the hydroxy group is in reactive esterified form, for example as described for process b. The reaction is carried out, for example, by reacting a compound of the formula VIII in nonactivated form with the reactive carboxylic acid or alcohol derivative, it being possible for the activation of the carboxylic acid also to take place in situ, in the presence of the compound of the formula VIII, for example in a manner analogous to that described for process a. Alternatively, the reaction may be carried out by reacting a compound of the formula VIII in which the hydroxy group(s) that participate(s) in the reaction is (are) present in reactive esterified form, for example in the form of a halide, with a carboxylic acid or an alcohol, each in non-activated form, or with a reactive carboxylic acid salt, for example in a manner analogous to that described for process a.

Process f

A nucleophilic leaving group X is especially a hydroxy group esterified by suitable acids, for example reactive esterified hydroxy as described for process b.

If in the compound of the formula X the radical T represents NH, the reaction is best carried out with the aid of a base, it being preferable to use equimolar amounts of the base. As bases there are used, especially, for example, metal hydroxides, carbonates or alcoholates, such as alkali metal or alkaline earth metal hydroxides or alcoholates, for example sodium or potassium hydroxide or sodium tert.-butoxide or alkali metal carbonates or salts, especially alkali metal salts, of secondary amides, for example 2-oxopyrrolidine-sodium or strongly basic ion exchangers, for example Dowex 1 (registered trade mark), also hydrides or amides, for example alkali metal hydrides or amides, such as sodium hydride or amide or lithium diisopropylamide.

The reaction is preferably carried out in an inert organic solvent, if desired or necessary while cooling or heating, for example in a temperature range of from approximately −80° C. to approximately +150° C., especially at from 0° C. to 100° C.

Activation with the aid of a base may be effected at the same temperature as the actual coupling reaction or at a different temperature.

Especially when using a very strong base, for example lithium diisopropylamide, activation with the base ("metallation") is effected at a lower temperature (for example −80° C.) than the coupling reaction. In this case for example, the reaction vessel may be allowed to warm up slowly once metallation is complete.

When the solvent is chosen, the type of base being used must also be taken into account. Reactions using alkali metal hydroxides are preferably carried out in dimethyl sulphoxide or in alcohols, such as lower alkanols, for example anhydrous ethanol, at the boiling temperature, and reactions using alcoholates are preferably carried out in ethers, especially cyclic ethers: using sodium-tert.-butoxide, for example in dioxan at room temperature. Reactions with, for example, 2-oxopyrrolidine-sodium, are carried out inter alia in a mixture of a cyclic ether and an aromatic hydrocarbon, for example a dioxan/toluene mixture, at a temperature of from room temperature to 60° C.

The reaction according to the invention with aid of an ion exchanger is carried out especially in an alcohol, for example a lower alkanol, for example ethanol, at room temperature.

A reactive derivative of a compound of the formula X in which the radical T represents oxygen is, for example, a suitable carboxylic acid salt, for example a caesium salt with high nucleophilicity of the carboxylate anion, or a silver salt, the silver ion forming with a halide X a sparingly soluble precipitate. In order to increase the nucleophilicity of the carboxylate anion, the ion of opposite charge may also be removed spatially, for example by the addition of complex formers, such as crown ethers, for example 18-crown-6. When using 18-crown-6 the reaction may be carried out using a potassium salt.

Possible protecting groups and their removal are described under process a.

Process g

Functional groups in a compound of the formula I that may be protected by a readily removable protecting group are especially the phosphoric acid group, a hydroxy group in the radical Z, free carboxy in the radical Y, or free amino, hydroxy, carboxy or mercapto in the radical $R^1$. Suitable protecting groups and their removal are described, for example, under process a and b.

Process h

A suitable enzyme is, for example, phospholipase $A_2$, which is commercially available (for example Boehringer AG, Mannheim, Federal Republic of Germany).

The starting materials required for carrying out the above-mentioned processes are known or may be manufactured by processes known per se, for example by a process analogous to one of those described hereinbefore.

The acylation of an amino or hydroxy group contained in the radical $R^1$ is carried out in a manner analogous to that described under process a.

The esterification of a carboxy group contained in the radical $R^1$ is carried out, for example, as follows:

Suitable agents are, for example, corresponding diazo compounds, such as optionally substituted diazolower alkanes, for example diazomethane, diazoethane, diazo-n-butane or diphenyldiazomethane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture and, depending on the diazo reagent, while cooling, at room temperature or while heating gently, also, if necessary, in a closed vessel and/or under an inert gas atmosphere, for example a nitrogen atmosphere.

Other suitable agents are esters of corresponding alcohols, especially those with strong inorganic or organic acids, such as mineral acids, for example hydrohalic acids, such as hydrochloric, hydrobromic or hydriodic acid, also sulphuric acid, or halosulphuric acid, for example fluorosulphuric acid, or strong organic sulphonic acids, such as optionally halosubstituted, such as fluorine-substituted, lower alkanesulphonic acids, or aromatic sulphonic acids, such as, for example, benzenesulphonic acids optionally substituted by lower alkyl, such as methyl, halogen, such as bromine and/or by nitro, for example methanesulphonic, trifluoromethanesulphonic or p-toluenesulphonic acid. Such esters are, inter alia, lower alkyl halides, di-lower alkyl sulphates, such as dimethyl sulphate, also fluorosulphonic acid esters, such as fluorosulphonic acid lower alkyl esters, for example fluorosulphonic acid methyl ester, or optionally halo-substituted methanesulphonic acid lower alkyl esters, for example trifluoromethanesulphonic acid methyl ester. They are customarily used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture thereof. It is preferable to use suitable condensation agents, such as alkali metal carbonates or bicarbonates, for example sodium or potassium carbonate or bicarbonate (customarily together with a sulphate), or organic bases, such as, customarily, sterically hindered tri-lower alkylamines, for example N,N-diisopropyl-N-ethylamine (preferably together with halosulphonic acid lower alkyl esters or optionally halo-substituted methanesulphonic acid lower alkyl esters), the reaction being carried out while cooling, at room temperature or while heating, for example at temperatures of from approximately $-20°$ C. to approximately $50°$ C., and, if necessary, in a closed vessel and/or in an inert gas atmosphere, for example, a nitrogen atmosphere.

Other agents are corresponding tri-substituted oxonium salts (so-called Meerwein salts) or disubstituted carbenium or halonium salts in which the substituents are the etherifying radicals, for example tri-lower alkyloxonium salts, and also di-lower alkoxycarbenium or di-lower alkylhalonium salts, especially the corresponding salts with complex fluorine-containing acids, such as the corresponding tetrafluoroborates, hexafluorophosphates, hexafluoroantimonates, or hexachloroantimonates. Such reagents are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These agents are preferably used in an inert solvent, such as an ether or a halogenated hydrocarbon, for example diethyl ether, tetrahydrofuran or methylene chloride, or in a mixture thereof, if necessary in the presence of a base, such as an organic base, for example a tri-lower alkylamine, preferably a sterically hindered tri-lower alkylamine, for example N,N-diisopropyl-N-ethylamine, and while cooling, at room temperature or while heating gently, for example at from approximately $-20°$ C. to approximately $50°$ C., if necessary in a closed vessel and/or in an inert gas atmosphere, for example a nitrogen atmosphere.

The conversion of free carboxy in a compound of the formula (I) into esterified carboxy may also be effected, for example, by reacting a compound of the formula (I) in which other functional groups that may be present are optionally in protected form, or a reactive functional carboxy derivative, including a salt, thereof, with a corresponding alcohol, for example in a manner analogous to that described for process a.

The processes described above, including the processes for removing protecting groups and the additional process steps, are carried out in a manner known per se, for example in the presence or absence of solvents and diluents, if necessary in the presence of condensation agents or catalysts, at reduced or elevated temperature, for example in a temperature range of from approximately $-20°$ C. to approximately $150°$ C., in a closed vessel and/or in an inert gas atmosphere, for example a nitrogen atmosphere.

Taking into account all the substituents in the molecule, there should be used, if necessary, for example if readily hydrolysable radicals are present, particularly mild reaction conditions, such as short reaction times, mild acidic or basic agents in a low concentration, stoichiometric quantity ratios, and suitable catalysts, solvents, temperature and/or pressure conditions should be chosen.

The invention also relates to those embodiments of the process in which a compound obtainable as intermediate at any stage of the process is used as starting material and the remaining process steps are carried out or the process is interrupted at any stage or a starting material is formed under the reaction conditions or is used in the form of a reactive derivative or salt. The starting materials used are preferably those which, according to the process, result in the compounds described above as being especially valuable.

The present invention also relates to novel starting materials and/or intermediates and to processes for their manufacture. The starting materials used and the reaction conditions chosen are preferably those which result in the compounds described in this Application as being especially preferred.

Mixtures of isomers may be separated into the individual isomers in a manner known per se, for example by fractional crystallisation, chromatography, etc., and racemates may be separated, for example, by forming derivatives with optically active compounds and separating the resulting diastereoisomeric mixtures into the optically active antipodes.

The invention also relates to pharmaceutical preparations containing an amount of the active ingredient effective for the prophylaxis or treatment of viral infections, optionally together with pharmaceutically acceptable carriers suitable for topical, for example intranasal, enteral, for example oral or rectal, or parenteral, administration, and may be inorganic or organic and solid or liquid. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colourings, flavourings and sweeteners. The pharmacologically active compounds of the present invention can also be used in the form of parenterally administrable preparations or in the form of infusion solutions. Such solutions are preferably isotonic aqueous solutions or suspensions, it being possible, for example in the case of lyophilised preparations that contain the active ingredient alone or together with a carrier, for example mannitol, for these to be manufactured before use. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilising processes, and contain approximately from 0.001% to 99%, especially from approximately 0.01% to approximately 10%, more especially from 0.1% to 5%, of the active ingredient(s), an active ingredient concentration of less than 1% being suitable especially for preparations that are to be applied topically.

As forms of administration for topical application the following are preferred: creams, ointments or pastes containing from 0.001% to 1%, especially from 0.01% to 0.1%, for example 0.05%, of active ingredient, for example ointments for intranasal administration or lipsticks, or aqueous solutions containing from 0.001% to 1%, especially from 0.05% to 0.5%, for example 0.1%, of active ingredient, preferably isotonic, sterile and physiologically tolerable solutions, for example eye drops, preferably in microcontainers for once-only use, or sprays for use in the mouth and throat area.

Especially suitable are the pharmaceutical preparations described in the Examples.

Creams are oil-in-water emulsions that contain more than 50% water. There are used as oily base especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable as emulsifiers are surface-active substances having predominantly hydrophilic properties, such as corresponding non-ionic emulsifiers, for example fatty acid esters of polyalcohols or ethylene oxide adducts thereof, such as polyglycerine fatty acid esters or polyoxyethylenesorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl alcohol or steryl alcohol. Additives to the aqueous phase are, inter alia, agents that reduce the drying-out of the creams, for example polyalcohols, such as glycerine, sorbitol, propylene glycol and/or polyethylene glycols, also preservatives, perfumes, etc.

Ointments are water-in-oil emulsions that contain up to 70%, but preferably from approximately 20% to approximately 50%, water or aqueous phase. Suitable as the fatty phase are especially hydrocarbons, for example petroleum jelly, paraffin oil and/or hard paraffins which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerine, propylene glycol, sorbitol and/or polyethylene glycol, and also preservatives, perfumes, etc.

Fatty ointments are anhydrous and contain as base especially hydrocarbons, for example paraffin, petroleum jelly and/or liquid paraffins, also natural or partially synthetic fats, for example coconut fatty acid triglyceride, or preferably hardened oils, for example hydrogenated groundnut or castor oil, also fatty acid partial esters of glycerine, for example glycerine mono- and di-stearate, and also, for example, the fatty alcohols increasing the water-absorption capacity, emulsifiers and/or additives mentioned in connection with the ointments.

Pastes are creams and ointments having secretion-absorbing powder constituents, such as metal oxides, for example titanium oxide or zinc oxide, also talc and/or aluminium silicates, the purpose of which is to bind any moisture or secretions present.

Foams are administered from pressurised containers and are liquid oil-in-water emulsions in aerosol form; halogenated hydrocarbons, such as chlorofluoro-lower alkanes, for example dichlorodifluoromethane and dichlorotetrafluoroethane, are used as propellants. There are used as the oily phase, inter alia, hydrocarbons, for example paraffin oil, fatty alcohols, for example cetyl alcohol, fatty acid esters, for example isopropyl myristate, and/or other waxes. There are used as emulsifiers, inter alia, mixtures of emulsifiers having predominantly hydrophilic properties, such as polyoxyethylenesorbitan fatty acid esters (Tweens), and emulsifiers with predominantly lipophilic properties, such as sorbitan fatty acid esters (Spans). The customary additives, such as preservatives, etc., are also added.

Tinctures and solutions generally have anaqueous-ethanolic base to which are added, inter alia, polyalcohols, for example glycerine, glycols and/or polyethylene glycol, as humectants for reducing evaporation, and fat-restoring substances, such as fatty acid esters with lower polyethylene glycols, that is to say lipophilic substances that are soluble in the aqueous mixture, as a replacement for the fatty substances removed from the skin by the ethanol, and, if necessary, other adjuncts and additives.

The manufacture of the topically administrable pharmaceutical preparations is carried out in a manner known per se, for example by dissolving or suspending the active ingredient in the base or, if necessary, in a part thereof. When processing the active ingredient as a solution, it is generally dissolved in one of the two phases before emulsification; when processing the active ingredient as a suspension, it is mixed with part of the base after emulsification and then added to the rest of the formulation.

The following Examples illustrate the invention without limiting it in any way. The $R_f$ values are determined on silica-gel thin-layer plates (Merck, Darmstadt, Germany). The ratio of the eluants in the eluant mixtures used is given in parts by volume (v/v), and temperatures are given in degress Celsius. The concentration, c, of the substance in the solvent (mixture) is given, in the case of optical rotation, as a percentage (weight-/volume).

Abbreviations boc = tert.-butoxycarbonyl
Me = methyl
MeOH = methanol
m.p. = melting point

EXAMPLE 1

29 g of N-boc-L-tyrosine-2-(1,2-dipalmitoyl-sn-glycero-3-hydroxyphosphoryloxy)-ethylamide . 0.67 H$_2$O (partly in the form of the sodium salt) are dissolved in a mixture of 40 ml of trifluoroacetic acid and 80 ml of methylene chloride and left to stand for 2.5 hours at room temperature. The solution is evaporated to dryness in vacuo, the residue is triturated 3 times with ice-water and a colourless suspension is obtained which is filtered with suction. The precipitate is crystallised twice from ethyl methyl ketone/isopropyl alcohol/water (1:1:1:). L-tyrosine-2-(1,2-dipalmitoyl-sn-glycero-3-hydroxyphosphoryloxy)-ethylamide is obtained in the form of colourless crystals having a decomposition point of 185°–200°; $[\alpha]_D^{20} = +39°$ (c=1.007; CHCl$_3$: MeOH:H$_2$O = 80:10:2), R$_f$=0.40 (CHCl$_3$:MeOH:-H$_2$O = 80:20:2). The starting material is obtained as follows:

Stage 1.1: 1.52 g (1.5 equivalents) of N-boc-L-tyrosine-N-hydroxysuccinimide ester and 0.422 ml of triethylamine are added at room temperature to 2 g of 2-(1,2-dipalmitoyl-sn-glycero-3-hydroxyphosphoryloxy)ethylamine (cephalin), dissolved in 30 ml of CHCl$_3$/MeOH/H$_2$O (80:20:2). After 18 hours at room temperature, the solution is evaporated to dryness in vacuo, the residue is taken up with ethyl acetate/tetrahydrofuran (7:2) and extracted by shaking once with 5% NaHCO$_3$ solution and twice with saturated NaCl solution. The combined aqueous phases are extracted once with ethyl acetate/tetrahydrofuran (7:2). After drying (Na$_2$SO$_4$) and concentration by evaporation of the organic phase, a crude product is obtained which is purified by chromatography over silica gel using CHCl$_3$/MeOH/H$_2$O (90:10:0.5). N-boc-L-tyrosine-2-(1,2-dipalmitoyl-sn-glycero-3-hydroxyphosphoryloxy)-ethylamide . 0.67 H$_2$O, partly in the form of the sodium salt, is obtained: m.p. 110°–112°, $[\alpha]_D^{20} = +8°$ (c=0.786; methanol), R$_f$=0.64 (CHCl$_3$:MeOH:H$_2$O = 80:20:2). Complete conversion into the sodium salt is effected by the filtration process described in Example 3.

EXAMPLE 2

From the sodium salt of N-boc-glycine-2-(1,2-dipalmitoyl-sn-glycero-3-hydroxyphosphoryloxy)ethylamide . 0.87 H$_2$O by a method analogous to that described in Example 1 involving cleavage with trifluoroacetic acid in methylene chloride there is obtained glycine-2-(1,2-dipalmitoyl-sn-glycero-3-hydroxyphosphoryloxy)-ethylamide . 0.13 H$_2$O; m.p. 220°–227° (decomposition), R$_f$=0.16 (CHCl$_3$:MeOH:H$_2$O = 80:20:2). The starting material is obtained as follows:

Stage 2.1: From 2-(1,2-dipalmitoyl-sn-glycero3-hydroxyphosphoryloxy)-ethylamine and N-boc-glycine-N-hydroxysuccinimide ester there is obtained, in a manner analogous to that described in Stage 1.1, the sodium salt of N-boc-glycine-2-(1,2-dipalmitoyl-sn-glycero-3-hydroxyphosphoryloxy)-ethylamide . 0.87 H$_2$O, m.p. 60°–65°, $[\alpha]_D^{20} = +5.9°$ (c=0.945, CHCl$_3$ MeOH = 1:1), R$_f$=0.37 (CHCl$_3$:MeOH:H$_2$O = 80:20:2).

EXAMPLE 3

4.7 g of the sodium salt of 2-(1,2-dipalmitoyl-sn-glycero-3-hydroxyphosphoryloxy)-ethylamine are dissolved in 80 ml of chloroform/methanol (9:1). A solution of 1.21 g of citric acid anhydride in 16 ml of absolute dimethylacetamide and then 1.9 ml of triethylamine are added thereto. After 2 hours at room temperature, the solution is evaporated to dryness in vacuo at 35°, the residue is stirred with 20 ml of 1N hydrochloric acid, and the resulting colourless crystals are filtered with suction. This is repeated, the crystals are washed with 1N hydrochloric acid, the filtered material is suspended in 200 ml of water and the pH value is adjusted to 6.8 while monitoring with an electrode. The substance dissolves completely. The solution is filtered in a stirred cell through an ultrafilter having an exclusion limit of 10,000 daltons (manufacturer: Amicon Corporation, Danvers, Mass., 0!932 U.S.A., model 402, Ultrafilter PM 10/76 mm diameter, inert, non-ionic polymers based on polysulphone, mean pore size 10 Å), until the material passing through the filter is free of chloride. The solution above the filter, containing the substance, is concentrated to 50 ml using a pressure of 2 bar and freeze-dried. The trisodium salt of 3,4-dicarboxy-3-hydroxybutyric acid [2-(1,2-dipalmitoyl-sn-glycero-3-hydroxyphosphoryloxy)ethyl]-amide . 2 H$_2$O is obtained in the form of a colourless product having a melting point of 80°–82° (decomposition); $[\alpha]_D^{20} = +8.3°$ (c=R$_f$=0.2 (CHCl$_3$:MeOH:phosphate buffer [disodium hydrogen phosphate/potassium dihydrogen phosphate; pH=7] = 70:30:5).

EXAMPLE 4

Groups of 30 female MF-2f SPF mice having a body weight of 14–16 g are infected intranasally under light narcosis with a mixture of equal parts of diethyl ether, ethanol and chloroform, with lethal doses (approximately LD$_{80-90}$; 1–4 plaque forming units [PFU]), in the form of 0.05 ml portions each, of a suspension of influenza A/Texas/1/77 (mouse-adapted strain) viruses.

At the point in time indicated below [days], based on the day of infection, the amounts indicated in Table 1 of the individual active ingredients in 0.05 (intranasal administration) and 0.2 ml, (oral administration) of a 0.005% by weight solution of the sodium salt of carboxymethylcellulose in twice-distilled, pyrogen-free water are administered once (single dose), in the manner indicated in Table 1, to 10 of these mice.

The remainder of the above-mentioned mice, that is to say 20, are used as a control, that is to say they receive a placebo (0.005% by weight solution of the sodium salt of carboxymethylcellulose).

The intranasal administration of the active ingredient is effected under light narcosis with a mixture of equal parts of diethyl ether, ethanol and chloroform.

Compound I=glycine-2-(1,2-dipalmitoyl-sn-glycero-3-hydroxyphosphoryloxy)-ethylamide; 0.13 H$_2$O; compound II=L-tyrosine-2-(1,2-dipalmitoyl-sn-glycero-3-hydroxyphosphoryloxy)-ethylamide; compound III=the trisodium salt of citric acid mono-2-(1,2-dipalmitoyl-sn-glycero-3-hydroxyposphoryloxy)-ethylamide. 2 H$_2$O; compound IV=L-alanine-2-(1,2-dipalmitoyl-sn-glycero-3-hydroxyphosphoryloxy)-ethylamide.

TABLE 1

| Active ingredient | Method of administration | Time of administration | Percentage of mice still living 23 days after infection, as a function of the amount of active ingredient [mg/kg], statistical significance *P $\leq$ 0.05, **P $\leq$ 0.01 (Vierfelder test) | | | | |
|---|---|---|---|---|---|---|---|
| | | | 10 | 1 | 0.1 | 0.01 | 0 = control |
| I | oral | +7 | | 70 | 60 | 80* | 30 |
| | intranasal | −7 | | 60 | 80** | 60 | 20 |
| II | oral | +7 | | 40 | 70 | 100** | 30 |
| | intranasal | −7 | | 60 | 90** | 90** | 20 |
| III | oral | +7 | 50 | 70* | 60 | | 20 |
| IV | oral | +7 | 90** | 90** | 90** | | 30 |
| | intranasal | −7 | | 100** | 80** | 50 | 20 |

EXAMPLE 5

3.80 g (3.53 mmol) of the triethylammonium salt of N$^\alpha$-benzyloxycarbonyl-N$^\epsilon$-tert.-butoxycarbonyl-L-lysine-2-(1,2-dipalmitoyl-sn-glvcero-3-hydroxyphosphoryloxy)-ethylamide are dissolved in 15 ml of absolute dioxan and, after cooling to 5°, cleaved by the addition of 24 ml of 33% hydrobromic acid in glacial acetic acid. The resulting reddish suspension is stirred for 30 minutes at 5°, and then concentrated and, after the addition of 50 ml of absolute dioxan, lyophilised. The residue is purified by chromatography twice over silica gel (Merck, type 60, particle size 0.063–0.200 mm; 1:130, 5 ml fractions) in chloroform/methanol/water (70:30:5). After concentration of the pure fractions by evaporation, the residue is dissolved in 60 ml of chloroform/methanol/water (70:30:5), sterile-filtered through a millipore filter (manufacturer: Millipore Corporation, Bedford, Mass., 01730 U.S.A., Teflon$^R$, type FGLP 0.2 μm) and caused to crystallise by the addition of 100 ml of absolute dioxan. L-lysine-2-[1,2-dipalmitoyl-sn-glycero-3-hyroxyphosphoryloxy]-ethylamide monohydrobromide. 0.9 H$_2$O is obtained in the form of needle-shaped crystals; m.p. 210°–212°, $[\alpha]_D^{20}=+2.9°$ and $[\alpha]_{546\ nm}^{20}=+4°$ (in each case c=0.700; chloroform:methanol:water=70:30:5), R$_f$=0.35 (chloroform:methanol:water:acetic acid=70:40:10:0.5), Rf=0.13 (chloroform:methanol:water=70:30:5). The starting material is obtained as follows:

Stage 5.1: 5.53 g (7.99 mmol) of 2-(1,2dipalmitoyl-sn-glycero-3-hydroxyphosphoryloxy)-ethylamine are suspended in 120 ml of chloroform/methanol/water (70:30:5) and dissolved by adding dropwise 1.23 ml (8.80 mmol) of triethylamine. To this solution 4.67 g (10.38 mmol) of N$^\alpha$-benzyloxycarbonyl-N$^\epsilon$-tert.-butoxycarbonyl-L-lysine-p-nitrophenyl ester, dissolved in 60 ml of dimethylformamide, are added dropwise. After stirring for 16 hours at room temperature, the slightly yellowish suspension is residue is eluted from the column over silica gel (Merck, type 60, particle size 0.063–0.200 mm; 1:50; 5 ml fractions), initially with chloroform and then with chloroform/methanol (9:1) and the pure fractions are collected. The triethylammonium salt of N$^{\alpha\text{-}benzyloxycarbonyl\text{-}N\epsilon}$$_5$-tert.-butoxycarbonyl-L-lysine-2(1,2-dipalmitoyl-sn-glycero-3-hydroxyphosporyloxy)ethylamide. 0.7 H$_2$O is obtained in the form of a colourless powder; $[\alpha]_D^{20}=+2.2°$ and $[\alpha]_{546nm}^{20}=+2.7°$ (in each case c=0.555; chloroform), R$_f$=0.61 (chloroform:methanol:water=70:30:5), R$_f$=0.82 (ethyl acetate:n-butanol:pyridine:acetic acid:-water=42:21:21:6:10).

EXAMPLE 6

Non-aqueous single dose for nasal administration

| Composition | |
|---|---|
| L-alanine-2-(1,2-dipalmitoyl-sn-glycero-3-hydroxyphosphoryloxy)-ethylamide | 0.03 mg |
| Miglyol 812 | 30.00 mg |

Manufacture 0.03 mg of the active ingredient are dissolved under aseptic conditions in 29.97 mg of Miglyol.

The resulting solution is introduced into a commercially available single administration nasal applicator, for example according to U.S. Pat. No. 3,739,951, which before use is set up on a propellant capsule.

EXAMPLE 7

Nasal drops

| Composition | I | II |
|---|---|---|
| L-alanine-2-(1,2-dipalmitoyl-sn-glycero-3-hydroxyphosphoryloxy)-ethylamide | 0.15 mg | 0.10 mg |
| Thiomersal | 0.02 mg | — |
| sodium monohydrogen phosphate.2H$_2$O | 0.30 mg | 0.30 mg |
| sodium dihydrogen phosphate.12H$_2$O | 10.10 mg | 10.10 mg |
| benzalkonium chloride | — | 0.10 mg |
| disodium salt of ethylenediamine-tetraacetic acid (EDTA) | 0.50 mg | 0.50 mg |
| sodium chloride | 3.70 mg | 4.50 mg |
| demineralised water | 988.30 mg | 987.60 mg |
| pH value: | 5.0 ± 0.3 | 5.0 ± 0.3 |
| reduction in freezing point | −0.51° C. | −0.56° C. |

Manufacture

While stirring, sodium dihydrogen phosphate, disodium hydrogen phosphate, sodium chloride, Thiomersal and the disodium salt of EDTA are dissolved at room temperature in part of the above-mentioned amount of demineralised water.

The active ingredient is then dissolved in the resulting solution and the rest of the demineralised water is added.

The solution or a part or multiple thereof is filtered through a membrane filter and introduced into purified containers. Suitable containers are, for example, (a) glass or plastics containers (5 ml or 10 ml) having a pipette made of glass or plastics with an elastomeric pipette bulbs, (b) compressible bottle made of plastics and having an ascending tube and a spray head made of plastics, (c) single-dose containers made of plastics (content 2–3 drops), or (d) glass or plastics bottles provided with a standardised pump-metering spray made of plastics (without propellant gas).

EXAMPLE 8

Nasal ointment

| Composition | |
|---|---|
| L-alanine-2-(1,2-dipalmitoyl-sn-glycero-3-hydroxyphosphoryloxy)-ethylamide | 0.03 g |
| paraffin oil, viscous | 20.00 g |
| white petroleum jelly | 30.00 g |
| wool fat, anhydrous | 40.00 g |
| demineralised water | 19.97 g |

Manufacture

The fatty phase, comprising paraffin oil, petroleum jelly and wool fat, is melted. The aqueous solution of the active ingredient is worked into the fatty phase at approximately 50° C.

EXAMPLE 9

Manufacture of 1000 tablets, containing 0.5% of active ingredient

| Composition per 1000 tablets: | |
|---|---|
| L-alanine-2-(1,2-dipalmitoyl-sn-glycero-3-hydroxyphosphoryloxy)-ethylamide | 0.5 g |
| lactose, ground | 43.0 g |
| corn starch | 52.0 g |
| Pharmacoat 603 ® (hydroxypropylmethyl-cellulose, containing 28–30% methoxy groups, supplied by Shinetsu Chemical Company, Tokyo, Japan) | 3.0 g |
| Aerosil ® (colloidal silica), supplied by Degussa, Frankfurt, Federal Republic of Germany) | 1.0 g |
| magnesium stearate | 0.5 g |

MANUFACTURE

The active ingredient and 15 g of lactose are premixed. The resulting pre-mixture is mixed with 28 g of lactose and 47 g of corn starch. A granulatable mass is manufactured with the resulting mixture and an aqueous solution of the Pharmacoat and the mass is then granulated, dried and ground. 5 g of corn starch, Aerosil and magnesium stearate are mixed with the ground material and the whole is compressed to form 1000 tablets each weighing 100 mg.

The compacts can be lacquered in a manner known per se so that they are resistant to gastric juices.

EXAMPLE 10

2 g of the sodium salt of N-benzyloxycarbonyl-L-aspartic acid α-benzyl ester 2-(1,2-dipalmitoyl-sn-glycero-3-hydroxyphosphoryloxy)-ethylamide are dissolved in chloroform/methanol/water (60:40:2) and hydrogenated with 2 g of Pd/BaSO$_4$ under normal pressure. The catalyst is filtered off and the filtrate is evaporated to dryness in vacuo. The residue is taken up with 100 ml of water and the pH value is brought to 7 with saturated NaHCO$_3$ solution. The resulting solution is filtered in a manner analogous to that described in Example 3 in an Amicon cell type 402 over an Ultrafilter Diaflo ® PM10 under a N$_2$ pressure of 2 bar and the filter supernatant is concentrated to approximately 50 ml. Then 300 ml of 10% NaCl solution are added and the whole is filtered with the addition of water until the filtrate is free of chloride. There is thus obtained, after freezedrying the supernatant, the sodium salt of L-aspartic acid β-2-(1,2-dipalmitoyl-sn-glycero-3-hydroxyphosphoryloxy)-ethylamide, which is obtained in pure form by digesting with warm dimethoxyethane; m.p. 197°–200° (decomposition), $R_f=0.36$, (CHCl$_3$:MeOH:H$_2$O=60:40:2), $R_f=0.11$ (CHCl$_3$:MeOH:H$_2$O=80:20:2). The starting material is obtained as follows:

In a manner analagous to that described in Stage 1.1, dipalmitoylcephalin is allowed to react with the β-N-hydroxysuccinimide ester of N-benzyloxycarbonylaspartic acid β-benzyl ester. After working up in a manner analogous to that described in Example 3, and chromatography over silica gel in CHCl$_3$/MeOH (9:1), the sodium salt of N-benzyloxycarbonyl-L-aspartic acid β-benzyl ester 2-(1,2-dipalmitoyl-sn-glycero-3-hydroxyphosphoryloxy)-ethylamide, which also contains traces of N-benzyloxycarbonylaspartic acid β-benzyl ester and can be used directly in the hydrogenation, is obtained; $R_f=0.54$ (CHCl$_3$:MeOH:H$_2$O=80:20:2).

EXAMPLE 11

By means of catalytic hydrogenation in a manner analogous to that described in Example 10, L-asparagine-α-2-(1,2-dilauroyl-sn-glycero-3-hydroxyphosphoryloxy)-ethylamide is obtained from the sodium salt of N-benzyloxycarbonyl-L-asparagine-α-2-(1,2-dilauroyl-sn-glycero-3-hydroxyphoshoryloxy)-ethylamide.

The starting material is obtained in a manner analogous to that described in Stage 1.1 from N-benzyloxycarbonylasparagine-N'-hydroxysuccinimide ester and dilauroylcephalin and by working up according to Example 3.

EXAMPLE 12

From the sodium salt of N-boc-D-alanine-2-(1,2-dipalmitoyl-sn-glycero-3-hydroxyphosphoryloxy)-ethylamide there is obtained, in a manner analogous to that described in Example 1, D-alanine-2-(1,2-dipalmitoyl-sn-glycero- 3-hydroxyphosphoryloxy)-ethylamide in the form of a hydrate;

$R_f=0.61$ (CHCl$_3$:MeOH:H$_2$O=70:30:5), $R_f=0.53$ (CHCl$_3$:MeOH:acetic acid:H$_2$O=75:27:0.5:5), $[\alpha]_D^\circ -14.1° \pm 1.2°$ (c=0.836; CHCl$_3$:MeOH:H$_2$O=70:30:2).

The starting material is obtained in the form of a sodium salt in a manner analogous to that described in Stage 1.1 and Example 3 from dipalmitoylcephalin and N-boc-D-alanine-N-hydroxysuccinimide ester; $R_f=0.5$ (CHCl$_3$:MeOH:H$_2$O=80:20:2).

EXAMPLE 13

Treatment of the triethylammonium salt of N-benzyloxycarbonyl-N,O-methylene-L-aspartic acid β-2-(1,2-dipalmitoyl-sn-glycero-3-hydroxyphosphoryloxy)-ethylamide with a mixture of 9 parts by volume of 3N HBr in glacial acetic acid and 1 part by volume of chloroform at room temperature for 3 hours leads to removal of the benzyloxycarbonyl group. The whole is diluted with dimethoxyethane, the pH value is adjusted to 7 using NaHCO$_3$ solution and the whole is diluted with 1 part by volume of water. The desired compound separates out and is filtered with suction and triturated twice with water at room temperature and three times with ethanol at 50° C., and in each case is cooled to room temperature and filtered with suction. N,O-methylene-D,L-aspartic acid β-2-(1,2-dipalmitoyl-sn-glycero-3-hydroxyphoshoryloxy)-ethylamide [=2-(1,3-oxazolidin-5-on-4-yl)-acetic acid 2-(1,2-dipalmitoyl-sn-glycero-3-hydroxyphosphoryloxy)-ethylamide] is thus obtained in the form of a hydrate; m.p. 174°–179°, $R_f=0.43$ (CHCl$_3$:MeOH:H$_2$O=70:30:3). The starting material is obtained as follows:

Stage 13.1: 6.3 g of N-benzyloxycarbonyl-N,O-methylene-L-aspartic acid (oxazolidinone derivative), 3.6 g of N-hydroxybenzotriazole and 5 g of N,N'-dicyclohexyl carbodiimide are dissolved in 90 ml of chloroform and stirred for 1.5 hours at room temperature. N,N'-dicyclohexylurea separates out and, in a manner analogous to that described in Example 1.1, a solution of 12 g of dipalmitoylcephalin and 5 ml of triethylamine in 400 ml of chloroform/isopropyl alcohol/water (70:30:0.3) is added to the resulting suspension. After 1 hour the reaction is complete. Working up is carried out in a manner analogous to that described in Example 3 and the sodium salt of N-benzyloxycarbonyl-N,O-methylene-D,L-aspartic acid β-2-(1,2-dipalmitoyl-sn-glycero-3-hydroxyphosphoryloxy)-ethylamide is obtained in the form of a colourless, crystalline hydrate; m.p. 94°–98°, $R_f=0.45$ (CHCl$_3$:MeOH:H$_2$O=80:20:2).

EXAMPLE 14

In a manner analogous to that described in Example 1 there is obtained from the sodium salt of N$^\alpha$N$^{im}$-di-boc-L-histidine-2-(1,2-didecanoyl-sn-glycero-3-hydroxyphosphoryloxy)-ethylamide with trifluoroacetic acid in methylene chloride, after working up in accordance with Example 3, L-histidine-2-(1,2-didecanoyl-sn-glycero-3-hydroxyphosphoryloxy)-ethylamide in the form of a hydrate.

The starting material is obtained in a manner analogous to that described in Stage 1.1 and Example 3 from N$^\alpha$,N$^{im}$-di-boc-L-histidine-N-hydroxysuccinimide ester and 2-(1,2-didecanoyl-sn-glycero-3-hydroxyphosphoryloxy)-ethylamine.

EXAMPLE 15

3.47 g (0.04 mol) of lithium bromide (purum, Fluka) are added to a solution of 9.69 g (0.01 mol) of N-boc-L-tyrosine-2-(1,2-dipalmitoyl-sn-glycero-3-methoxyphosphoryloxy)-ethylamide in 100 ml of acetone, and the whole is heated for 3 hours under reflux while stirring.

The product that separates out after cooling in an ice-bath is filtered with suction and washed with cold acetone.

The lithium salt of N-boc-L-tyrosine-2-(1,2-dipalmitoyl-sn-glycero-3-hydroxyphosohoryloxy)-ethylamide is obtained in the form of a colourless powder that also contains 0.7 mol of water; $R_f=0.68$ (chloroform:methanol:water=80:20:2). The starting material is obtained as follows:

In a manner analogous to that described in Example 1 there is obtained from 7.06 g (0.01 mol) of 2-(1,2-dipalmitoyl-sn-glycero-3-methoxyphosphoryloxy)-ethylamine (cephalin methyl ester) and 5.46 g (1.5 equivalents) of N-boc-L-tyrosine-N-hydroxysuccinimide ester, N-boc-L-tyrosine-2-(1,2-dipalmitoyl-sn-glycero-3-methoxyphosphoryloxy)-ethylamide; $R_f=0.85$ (chloroform:methanol:water=80:20:2).

EXAMPLE 16

From the sodium salt of phosphoric acid [2-(N-boc-L-tyrosylamido)-ethyl]-monoester there is obtained in known manner [H.-J. Rüger, P. Kertscher and P. Nuhn, Pharmazie 34, 287 (1979); R. Aneja, J. S. Chadha and A. P. Davies, Tetrahedron Letters 48, 4183 (1969)] by reaction with 1,2-dipalmitoyl-sn-glycerine in absolute pyridine in the presence of 2,4,6-triisopropylbenzenesulphonic acid chloride (TPS) a the condensation agent, the sodium salt of N-boc-L-tyrosine-2-(1,2-dipalmitoyl-sn-glycero-3-hydroxyphosphoryloxy)-ethylamide; m.p. 110°–112°, $R_f=0.64$ (CHCl$_3$:MeOH:H$_2$O=80:20:2).

EXAMPLE 17

From the sodium salt of N-boc-L-tyrosine-2-(1,2-dipalmitoyl-sn-glycero-3-hydroxyphosphoryloxy)-ethylamide (4.27 mmol), by cleaving with phospholipase A$_2$ (0.mg; from pigs kidneys; Boehringer, Mannheim, Germany) at 50° and at a pH of 8 in the presence of 5.26 mmol of calcium chloride dihydrate in a well-stirred mixture of 369 ml of water and 331 ml of diisopropyl ether, there is obtained the calcium salt (.½ Ca$^{2+}$) of N-boc-L-tyrosine-2-(1-palmitoyl-sn-glycero-3-hydroxyphoshoryloxy)-ethylamide, which can be esterified in the 2-position in known manner with other fatty acids by the Steglich method [G. Höfle, W. Steglich and H. Vorbrüggen, Angew. Chem. 90, 602 (1978); cyclohexyl carbodiimide/4-dimethylamino pyridine].

EXAMPLE 18

0.5 g of the sodium salt of N-benzyloxycarbonyl-L-glutamic acid γ-tertiary-butyl ester α-2-(1,3-dipalmitoylglycero-2-hydroxyphosphoryloxy)-ethylamide is dissolved in a mixture of 4 ml of trifluoroacetic acid and 6 ml of methylene chloride and left to stand for 2 hours at 22°. The solution is concentrated by evaporation in vacuo and the residue is digested several times with petroleum ether/diethyl ether (2:1). The resulting pulverulent residue is dissolved in 10 ml of CHCl$_3$/MeOH/H$_2$O (75:25:5) and hydrogenated in the presence of palladium-on-barium sulphate. When the absorption of hydrogen is complete, the catalyst is filtered off and the filtrate is concentrated by evaporation in vacuo. After digesting with icewater, pulverulent L-glutamic acid α-2-(1,3-dipalmitoylglycero-2-hydroxyphosphoryloxy)-ethylamide is obtained. The starting material is obtained as follows:

Stage 18.1: To a solution of 2 g of 2-(1,3-dipalmitoylglycero-2-hydroxyphosphoryloxy)-ethylamine in 30 ml of CHCl$_3$/MeOH/H$_2$O (80:20:2) there are added, at 22°, 1.3 g of N-benzyloxycarbonyl-L-glutamic acid α-1-hydroxybenzotriazole ester γ-tertiary-butyl ester and 0.42 ml of triethylamine. After 17 hours at 22° the whole is concentrated by evaporation in vacuo, the residue is taken up in ethyl acetate/acetone (4:1) and shaken with 5% sodium bicarbonate solution. The phases are separated and the organic phase is washed twice with saturated sodium chloride solution. The aqueous phases are again extracted with ethyl acetate/acetone (4:1) and the organic phases are dried (sodium sulphate) and concentrated by evaporation. The residue is chromatographed over silica gel. The fractions eluted with $CHCl_3/MeOH/H_2O$ (85:15:0.5) contain N-carboxy-L-glutamic acid γ-tertiary-butyl ester α-2-(1,3-dipalmitoyl-glycero-2-hydroxyphosphoryloxy)-ethylamide.

EXAMPLE 19

In accordance with Example 18, the protecting groups in the sodium salt of N-benzyloxycarbonyl-L-glutamic acid α-tertiary-butyl ester γ-2-(1,3-dilauroyl-glycero-2-hydroxyphosphoryloxy)-ethylamide are removed, L-glutamic acid γ-2-(1,3-dilauroylglycero-2-hydroxyphosphoryloxy)-ethylamide being obtained.

The starting material is manufactured in a manner analogous to that described in Stage 18.1 from 2-(1,3-dilauroylglycero-2-hydroxyphosphoryloxy)-ethylamine and N-benzyloxycarbonylglutamic acid α-tertiary-butyl ester γ-1-hydroxybenzotriazole ester.

EXAMPLE 20

In a manner analogous to that described in Example 18, the benzyloxycarbonyl group in the sodium salt of N-benzyloxycarbonyl-L-glutamic acid γ-methyl ester α-2-(1,2-dipalmitoyl-sn-glycero-3-hydroxyphosphoryloxy)-ethylamide is removed by hydrogenation and L-glutamic acid γ-methyl ester α-2-(1,2-dipalmitoyl-sn-glycero-3-hydroxyphosphoryloxy)-ethylamide is obtained.

The starting material is manufactured in accordance with Stage 18.1 from 2-(1,2-dipalmitoyl-sn-glycero-3-hydroxyphosphoryloxy)-ethylamine and N-benzyloxycarbonyl-L-glutamic acid α-1-hydroxybenzotriazole ester γ-methyl ester.

EXAMPLE 21

There is obtained from the sodium salt of N-boc-L-tyrosine-2-(1-palmitoyloxypropyl-3-oxy-hydroxyphosphoryloxy)-ethylamide, when the boc group is removed in a manner analogous to that described in Example 1, L-tyrosine-2-(1-palmitoyloxypropyl-3-oxy-hydroxyphosphoryloxy)-ethylmide.

The starting material is obtained in accordance with Stage 1.1 from 2-(1-palmitoylpropyl-3-oxyhydroxyphosphoryloxy)-ethylamine and N-boc-L-tyrosine-N-hydroxysuccinimide ester.

EXAMPLE 22

In a manner analogous to that described in Example 1 there is obtained from the sodium salt of N-boc-L-serine- 2-(1,2-dihexadecyl-sn-glycero-3-hydroxyphosphoryloxy)-ethylamide, by treatment with trifluoroacetic acid, L-serine-2-(1,2-dihexadecyl-sn-glycero-3-hydroxyphosphoryloxy)-ethylamide. The starting material is obtained as follows:

Stage 22.: 2 g of boc-L-serine, 6.6 g of 2-(1,2-dihexadecyl-sn-glycero-3-hydroxyphosphoryloxy)ethylamine and 1.3 ml of triethylamine are dissolved in 35 ml of N,N-dimethylformamide and 2.7 g of 1-hydroxybenzotriazole and, at 0°, 2.3 g of N,N'-dicyclohexylcarbodiimide are added thereto. The whole is stirred for 2 hours at 0°, left to stand overnight at room temperature and then filtered. The filtrate is concentrated by evaporation in vacuo and worked up as in Stage 18.1 with ethyl acetate/acetone (4:). N-boc-L-serine-2-(1,2-dihexadecyl-sn-glycero-3-hydroxyphosphoryloxy)-ethylamide is obtained.

EXAMPLE 23

In accordance with Example 1, when the sodium salt of N-boc-L-proline-2-(1,2-didecanoyl-sn-glycero-3-hydroxyphosphoryloxy)-ethylamide is treated with trifluoroacetic acid, L-proline-2-(1,2-didecanoyl-sn-glycero-3-hydroxyphosphoryloxy)-ethylamide is obtained.

The starting material is obtained in a manner analogous to that described in Stage 18.1 from N-boc-L-proline-1-hydroxybenzotriazole ester and 2-(1,2-didecanoyl-sn-glycero-3-hydroxyphosphoryloxy)-ethylamine.

EXAMPLE 24

To 3.1 g (0.005 mol) of 0-(1,3-dilauroylglycero-2-hydroxyphosphoryl)-L-serine in 50 ml of chloroform there are added 0.8 ml of triethylamine and 2.56 g (1.9 equivalents) of N-acetyl-L-leucine-N'-hydroxysuccinimide ester in 10 ml of chloroform. After 3 hours at room temperature the solution is concentrated by evaporation in vacuo and worked up in a manner analogous to that described in Example 3. The sodium salt of N-acetyl-L-leucyl-0-(1,3-dilauroylglycero-2-hydroxyphosphoryl)-L-serine is obtained in the form of a colourless powder.

EXAMPLE 25

To 3.45 g (0.005 mol) of 0-(1,2-dioleoyl-sn-glycero-3-hydroxyphosphoryl)-L-serine in 50 ml of chloroform are added, at room temperature, 1 ml of triethylamine and 3 g of N-boc-L-leucine-N-hydroxysuccinimide ester. After 4 hours, the whole is concentrated by evaporation in vacuo and worked up in accordance with Example 3 to form the sodium salt of N-boc-L-leucyl-0-(1,2-dioleoyl-sn-glycero-3-hydroxyphosphoryl)-L-serine.

This compound is cleaved in accordance with Example 1 with trifluoroacetic acid in methylene chloride to form L-leucine-0-(1,2-dioleoyl-sn-glycero-3-hydroxyphosphoryl)-L-serine.

EXAMPLE 26

To a suspension of 0.8 g of 2-(1,2-dipalmitoyl-sn-glycero-3-hydroxyphosphoryloxy)-ethylamine in 200 ml of $CHCl_3$ there are added, at 22°, 0.5 ml of triethylamine and, after stirring for 15 minutes, 0.23 ml of benzoyl chloride. After stirring for two hours at 22°, the solution, which is now clear, is concentrated to a small volume, 3.5 ml of a 3-molar solution of the sodium salt of 2-ethylhexanoic acid in methanol are added, and the whole is concentrated to dryness by evaporation. The whole is chromatographed over 100 g of silica gel and eluted with $CHCl_3/MeOH$ (7:3). The oily product is dissolved in 20 ml of acetone at approximately 40° and cooled to 0°. The sodium salt of benzoic acid (1,2-dipalmitoyl-sn-glycero-3-hydroxyphosphoryloxy)-ethylamide crystallises; m.p. 60°–61°, $R_f$=0.68 ($CHCl_3:MeOH:H_2O$=60:40:3).

We claim:

1. A phosphatidyl compound of formula I

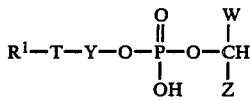

(I)

wherein
- $R^1$ is an alpha-amino-lower alkanoyl the alpha-amino group of which may be substituted by lower alkanoyl, by lower alkoxycarbonyl or by benzyloxycarbonyl and said alpha-amino-lower alkanoyl radical is substituted by phenyl or by 4-hydroxyphenyl;
- T is NH that is unsubstituted or substituted by lower alkyl, or is oxygen;
- Y is dimethylene which is unsubstituted or substituted by carboxy, lower alkoxycarbonyl, phenoxycarbonyl, benzyloxycarbonyl, benzhydryloxycarbonyl, carbamoyl or N-lower alkylcarbamoyl that is unsubstituted or is substituted in the lower alkyl moiety by carboxy or lower alkoxycarbonyl; and
- (a) W is hydrogen and
  Z is 1,2-dihydroxyethyl, 2-hydroxyethyl, or hydroxymethyl wherein at least one of the hydroxy groups is esterified by an aliphatic $C_8$–$C_{30}$ carboxylic acid or is etherified by an aliphatic $C_8$–$C_{30}$ alcohol or
- (b) each of W and Z is hydroxymethyl that is esterified by an aliphatic $C_8$–$C_{30}$ carboxylic acid or etherified by an aliphatic $C_8$–$C_{30}$ alcohol; or a pharmaceutically acceptable salt thereof or a mixture of said pharmaceutically acceptable salt and said compound.

2. The compound, pharmaceutically acceptable salt, or mixture thereof according to claim 1 wherein W is hydrogen and Z is 1,2-dihydroxyethyl wherein at least one of the hydroxy groups is esterified by a $C_8$–$C_{30}$ carboxylic acid.

3. The compound, pharmaceutically acceptable salt, or mixture thereof according to claim 1 wherein
- $R^1$ is α-amino-lower alkanoyl which is substituted by phenyl or by 4-hydroxyphenyl;
- T is NH or oxygen;
- Y is dimethylene which is unsubstituted or is substituted by carboxy, by lower alkoxycarbonyl, or by carbamoyl; and
  (a) W is hydrogen and Z is 1,2-dihydroxy ethyl esterified by a $C_{12}$–$C_{24}$ alkanoic or alkenoic acid at the 2-hydroxy position or at both the 1 and 2 hydroxy positions; or
  (b) each of W and Z are hydroxymethyl esterified by a $C_{12}$–$C_{24}$ alkanoic or alkenoic acid.

4. The pharmaceutically acceptable salt of claim 1 wherein $R^1$ is an α-amino-alkanoyl having up to 7 carbon atoms which is substituted by 4-hydroxyphenyl.

5. The compound, pharmaceutically acceptable salt, or mixture thereof of claim 1 wherein $R^1$ is the acyl radical of L-phenylalanine or L-tyrosine.

6. The pharmaceutically acceptable salt of claim 3 wherein $R^1$ is the acyl radical of L-phenylalanine or L-tyrosine.

7. The pharmaceutically acceptable salt of claim 1 wherein $R^1$ is L-tyrosine, the amino group of which is unsubstituted or substituted by t-butoxycarbonyl, by benzyloxycarbonyl or by lower alkanoyl;
- T is NH;
- Y is dimethylene which is unsubstituted by carboxy or lower alkoxycarbonyl; and
  (a) W is hydrogen and Z is 1,2-dihydroxyethyl, 2-hydroxyethyl, or hydroxymethyl wherein at least one hydroxy group is esterified by a $C_{10}$–$C_{18}$ alkanoic or $C_{18}$ alkenoic acid; or
  (b) each of W and Z is hydroxymethyl which is esterified by a $C_{10}$–$C_{18}$ alkanoic or $C_{18}$ alkenoic acid.

8. The pharmaceutically acceptable salt of claim 1 wherein
- $R^1$ is the acyl radical of L-tyrosine;
- T is NH;
- Y is dimethylene which is unsubstituted or substituted by carboxy.
- W is hydrogen; and
- Z is 1,2-dihydroxy ethyl in which each hydroxy group is esterified by a straight chain $C_{16}$–$C_{24}$-alkanoic or -alkenoic acid having an even number of carbon atoms.

9. The pharmaceutically acceptable salt of claim 1 wherein Y is dimethylene.

10. The pharmaceutically acceptable salt of claim 1 wherein each of W and Z is hydroxymethyl which is esterified by a $C_{12}$–$C_{18}$ alkanoic acid or by a $C_{18}$ alkenoic acid.

11. The pharmaceutically acceptable salt of claim 9 wherein T is NH.

12. A pharmaceutically acceptable salt of claim 1.

13. The pharmaceutically acceptable salt of claim 11 wherein $R^1$ is the acyl radical of L-tyrosine, N-lower alkoxycarbonyl L-tyrosine, or N-lower alkanoyl-L-tyrosine.

14. The compound of claim 1 which is L-tyrosine-2-(1,2-dipalmitoyl-sn-glycero-3-hydroxyphosphoryloxy)-ethylamide or a pharmaceutically acceptable salt thereof.

15. A pharmaceutical composition for the prophylaxis or treatment of a viral infection comprising a therapeutically effective amount of a compound of claim 1, a pharmaceutically salt therof, or mixture of said compound and said pharmaceutically acceptable salt; together with a pharmaceutically acceptable carrier.

16. A method for the prophylaxis or treatment of a viral infection in a warm blooded animal in need thereof comprising administering to said animal a therapeutically effective amount of a compound or pharmaceutically acceptable salt thereof according to claim 1.

17. The composition of claim 15 which is in a form selected from a tablet, capsule, isotonic parenteral or infusion solution or suspension, cream, ointment, paste, foam, tincture, and lipstick.

18. The composition of claim 15 wherein said compound or pharmaceutically acceptable salt thereof is L-tyrosine-2-(1,2-dipalmitoyl-sn-glycero-3-hydroxyphosphoryloxy)-ethylamide or a pharmaceutically acceptable salt thereof.

19. The method of claim 16 wherein said compound or pharmaceutically acceptable salt thereof is L-tyrosine-2-(1,2-di-palmitoyl-sn-glycero-3-hydroxyphosphoryloxy)-ethylamide or a pharmaceutically acceptable salt thereof.

* * * * *